United States Patent
Williams et al.

(10) Patent No.: US 11,532,377 B2
(45) Date of Patent: Dec. 20, 2022

(54) SYSTEMS AND METHODS FOR MODELING A PROTEIN PARAMETER FOR UNDERSTANDING PROTEIN INTERACTIONS AND GENERATING AN ENERGY MAP

(71) Applicant: Rutgers, The State University of New Jersey, New Brunswick, NJ (US)

(72) Inventors: Lawrence Williams, Belle Mead, NJ (US); Brian Schendt, Somerville, MA (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 615 days.

(21) Appl. No.: 16/496,577

(22) PCT Filed: Mar. 23, 2018

(86) PCT No.: PCT/US2018/024177
§ 371 (c)(1),
(2) Date: Sep. 23, 2019

(87) PCT Pub. No.: WO2018/175986
PCT Pub. Date: Sep. 27, 2018

(65) Prior Publication Data
US 2020/0286581 A1 Sep. 10, 2020

Related U.S. Application Data

(60) Provisional application No. 62/475,727, filed on Mar. 23, 2017.

(51) Int. Cl.
*G16B 15/00* (2019.01)
*G16B 45/00* (2019.01)
*C12N 9/36* (2006.01)

(52) U.S. Cl.
CPC ............ *G16B 15/00* (2019.02); *G16B 45/00* (2019.02); *C12N 9/2462* (2013.01); *C12Y 302/01017* (2013.01)

(58) Field of Classification Search
None
See application file for complete search history.

(56) References Cited

U.S. PATENT DOCUMENTS

2003/0130797 A1* 7/2003 Skolnick ............... G16B 15/00
702/19

OTHER PUBLICATIONS

C.A. Floudas: "Computational Methods in Protein Structure Prediction", Biotechnology Bioengineering, Jun. 1, 2007, vol. 97, No. 2, pp. 207-213.
Yousef, et al: "A Novel Method Based on Physicochemical Properties of Amino Acids and One Class Classification Algorithm for Disease Gene Identification", Journal of Biomedical Informatics, Aug. 2015, vol. 56, pp. 300-306.
Eyal, et al: "Importance of Solvent Accessibility and Contact Surfaces in Modeling Side-Chain Confirmations in Proteins", J. Comput Chem, Apr. 15, 2004, vol. 25, No. 5, pp. 712-724.
Iqbal, et al: "Estimation of Position Specific Energy as a Feature of Protein Residues from Sequence Alone for Structural Classification", PLOS One, Sep. 2, 2016, vol. 11, No. 9, pp. 1-23.

* cited by examiner

*Primary Examiner* — Suzanne M Noakes
*Assistant Examiner* — Jae W Lee
(74) *Attorney, Agent, or Firm* — Fox Rothschild LLP

(57) ABSTRACT

Systems and methods for modeling a three-dimensional protein structure are disclosed. The method includes receiving a primary amino acid sequence of a three-dimensional protein, translating the primary amino acid sequence to a first vector, determining a per-residue conformation index for each amino acid residue in the primary amino acid sequence, determining a vector set for each amino acid residue in the primary amino acid sequence, and using the per-residue interaction vector set to generate a multi-dimensional matrix for the three-dimensional protein structure. The first vector includes a unique numerical descriptor value corresponding to each amino acid residue in the primary amino acid sequence. The vector set includes a plurality per-residue interaction factors corresponding to a plurality of conformation indexes for that amino acid residue.

17 Claims, 14 Drawing Sheets

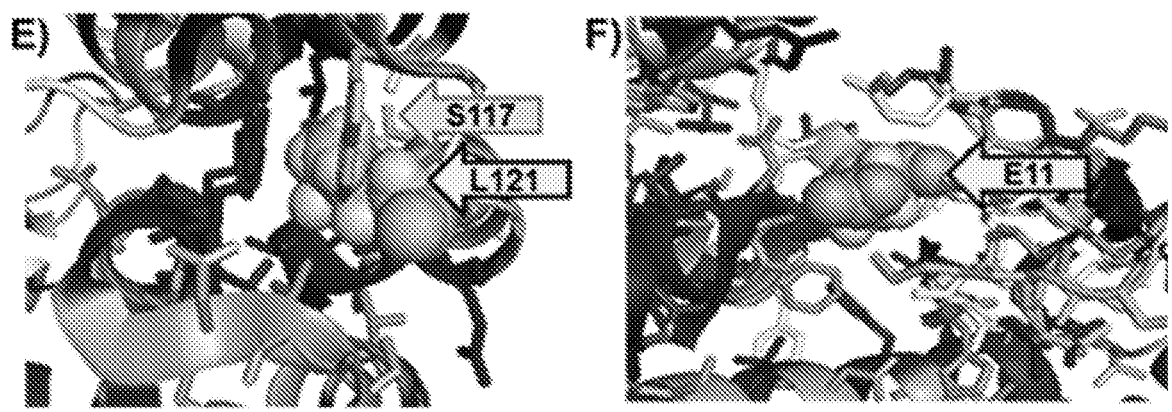
FIG. 7 (Contd.)

SYSTEMS AND METHODS FOR MODELING A PROTEIN PARAMETER FOR UNDERSTANDING PROTEIN INTERACTIONS AND GENERATING AN ENERGY MAP

CROSS-REFERENCE TO RELATED APPLICATIONS

This application claims priority under 35 U.S.C. § 119(e) to U.S. Provisional Patent Application No. 62/475,727, filed Mar. 23, 2017, the disclosure of which is incorporated by reference herein.

FIELD OF THE INVENTION

The present invention relates to a computer-implemented method and system for modeling the three-dimensional structure of a protein, and, more specifically, to generating an energy map for peptides and/or proteins given the amino acid sequence and a per-residue conformation index.

BACKGROUND

Biological processes are fundamentally realized at the atomic and molecular level. With few exceptions they are carried out by proteins. A protein is a biopolymer in which anywhere from about fifty to several thousand amino acids may be connected together by peptide bonds, typically in a linear sequence that is referred to as the primary structure of a protein. Under physiological conditions, each protein spontaneously folds into a unique three-dimensional structure, known as the tertiary structure of a protein. Shorter domains of regularly folded sequences (alpha helices, beta sheets, and reverse turns) form the secondary structure of a protein. Contemporary science is teeming with protein studies and derived technologies. For example, the biotechnology industry is dominated by proteins and has swollen to a conservatively estimated 2% of the US GDP. The largest contributors are biologics ($91B), crops and seeds ($128B), and biofuels, enzymes, biomaterials, and biochemical industrial products (>$105B). Despite this tremendous success, the biotechnology growth rate is significantly inhibited because its foundational molecular sciences lack a theory that qualitatively and quantitatively rationalizes—in tangible and direct terms—the relationship between primary sequence and protein structure and function. The native conformation of a protein, the tertiary structure, is closely related to its biological function. Hence, the prediction of protein conformation is not only of theoretical interest but is also of great importance for various applications and studies such as design of drugs, protein mutation studies, protein folding and engineering, or the like.

Consequently, such applications have grown to rely heavily on intelligent guesswork made possible by genomics, proteomics, informatics, and powerful experimental tools for mutagenesis and structure determination. Traditionally, methods of characterizing protein energetics rely heavily on all-atom computations informed by quantum mechanics. In the all-atom approach, the conformational energy is described as a mathematical function of geometrical variables inside the protein. However, such algorithms are computationally demanding and have been unable to provide qualitative guidelines, intuitive understanding, or energy-based (rather than informatics-based) predictive tools. Instead, the most computational models rely on large numbers of weak interactions to describe protein energetics. The difficulty may correspond to identifying governing principles of protein behavior due to obscuring details not yet clarified or may be intrinsic to all-atom calculations. For example, one challenge of folding a protein, through computer modeling and simulations using quantum mechanics, lies in finding the global minimum of the protein conformational energy landscape. There is sufficient experimental and theoretical evidence that the folded structure, or the native state, corresponds to a region close to the global energy minimum.

Thus, there is a need for improved and/or complementary analysis tools for understanding, predicting, and designing protein and/or peptide behavior, intra- and inter-protein interactions, and the three-dimensional structure of proteins based on the primary amino acid sequence.

SUMMARY

Systems and methods for modeling a three-dimensional protein structure are disclosed. In an embodiment, the method may include receiving a primary amino acid sequence of a three-dimensional protein, translating the primary amino acid sequence to a first vector, determining a per-residue conformation index for each amino acid residue in the primary amino acid sequence, determining a vector set for each amino acid residue in the primary amino acid sequence, and using the per-residue interaction vector set to generate a multi-dimensional matrix for the three-dimensional protein structure. The first vector may include a unique numerical descriptor value corresponding to each amino acid residue in the primary amino acid sequence. The vector set may include a plurality per-residue interaction factors corresponding to a plurality of conformation indexes for that amino acid residue. In an embodiment, the first vector may be a scale-invariant vector.

Optionally, the vector set for an amino acid residue in the primary amino acid sequence is a function of the numerical descriptor value and the per-residue conformation index of that amino acid. Additionally and/or alternatively, the vector set for the amino acid residue may also be a function of a normalization length of the protein. Optionally, the normalization length may be equal to 10.

In an embodiment, the numerical descriptor value corresponding to each amino acid residue in the primary amino acid sequence may be determined as a function of a solvent accessible surface area of that amino acid residue. Optionally, the numerical descriptor value may be a fractal exponent value.

In an embodiment, translating the primary amino acid sequence to the first vector may include replacing each amino acid residue in the primary amino acid sequence with a corresponding numerical descriptor value.

In one or more embodiments, the per-residue conformation index for each amino acid residue in the primary amino acid sequence may be used to represent a the Closest-Linked Nearest Neighbors (cINN) relationship for that amino acid residue. The per-residue conformation index for each amino acid residue in the primary amino acid sequence may have a value of 1, 2, 3, or 4.

In at least one embodiment, the multi-dimensional matrix may include a plurality of per-residue interaction factors corresponding to one or more amino acids in the primary amino acid sequence and representing all conformations of the primary amino acid sequence. Optionally, the multi-dimensional matrix may be a 4-dimensional matrix.

In an embodiment, the method may also include determining a free energy of one or more interacting pairs of amino acid residues in the primary amino acid sequence. Optionally, determining the free energy of the one or more interacting pairs of amino acid residues in the primary amino acid sequence may include determining the free energy as a function of the per-residue interaction vector set corresponding to each of the amino acid residues of an interacting pair of amino acids.

In some embodiments, the method may also include modeling the three-dimensional protein structure as a function of a plurality of vector sets corresponding to amino acid residues in the primary amino acid sequence and/or the free energy of one or more interacting pairs of amino acid residues in the primary amino acid sequence. Optionally, the method may include generating a graphical representation of the modeled three-dimensional protein structure.

In an embodiment, the graphical representation may be a plot of per-residue interaction factors of the primary amino acid sequence for a structural configuration of the three-dimensional protein. In an embodiment, generating a plot may include selecting a plurality of per-residue interaction factors from the multi-dimensional matrix based on the structural configuration, and using the selected plurality of per-residue interaction factors to generate the plot. Each of the amino acid residues of the primary amino acid sequence may also be classified into one of two or more categories based on a corresponding value of the per-residue interaction factor.

In at least one embodiment, the graphical representation may be also be an energy map for a structural configuration of the three-dimensional protein. The structural configuration may be a native configuration of the three-dimensional protein.

In an embodiment, the method may also include using the modeled three-dimensional protein structure to determine a structure of the three-dimensional protein that has enhanced stability and/or for engineering a new protein configured to bind to a target molecule.

In an embodiment, the method for modeling a three-dimensional protein may include receiving a primary amino acid sequence of a three-dimensional protein, translating the primary amino acid sequence to a first vector, determining a per-residue conformation index for each amino acid residue in the primary amino acid sequence, determining a vector set for each amino acid residue in the primary amino acid sequence, and using the per-residue interaction vector set to generate a multi-dimensional matrix for the three-dimensional protein structure. The first vector may include a unique numerical descriptor value corresponding to each amino acid residue in the primary amino acid sequence. The vector set may include a plurality per-residue interaction factors corresponding to a plurality of conformation indexes for that amino acid residue. The method may also include using the multi-dimensional matrix to determine a structure of the three-dimensional protein that has enhanced stability.

DETAILED DESCRIPTION

Figure 1:
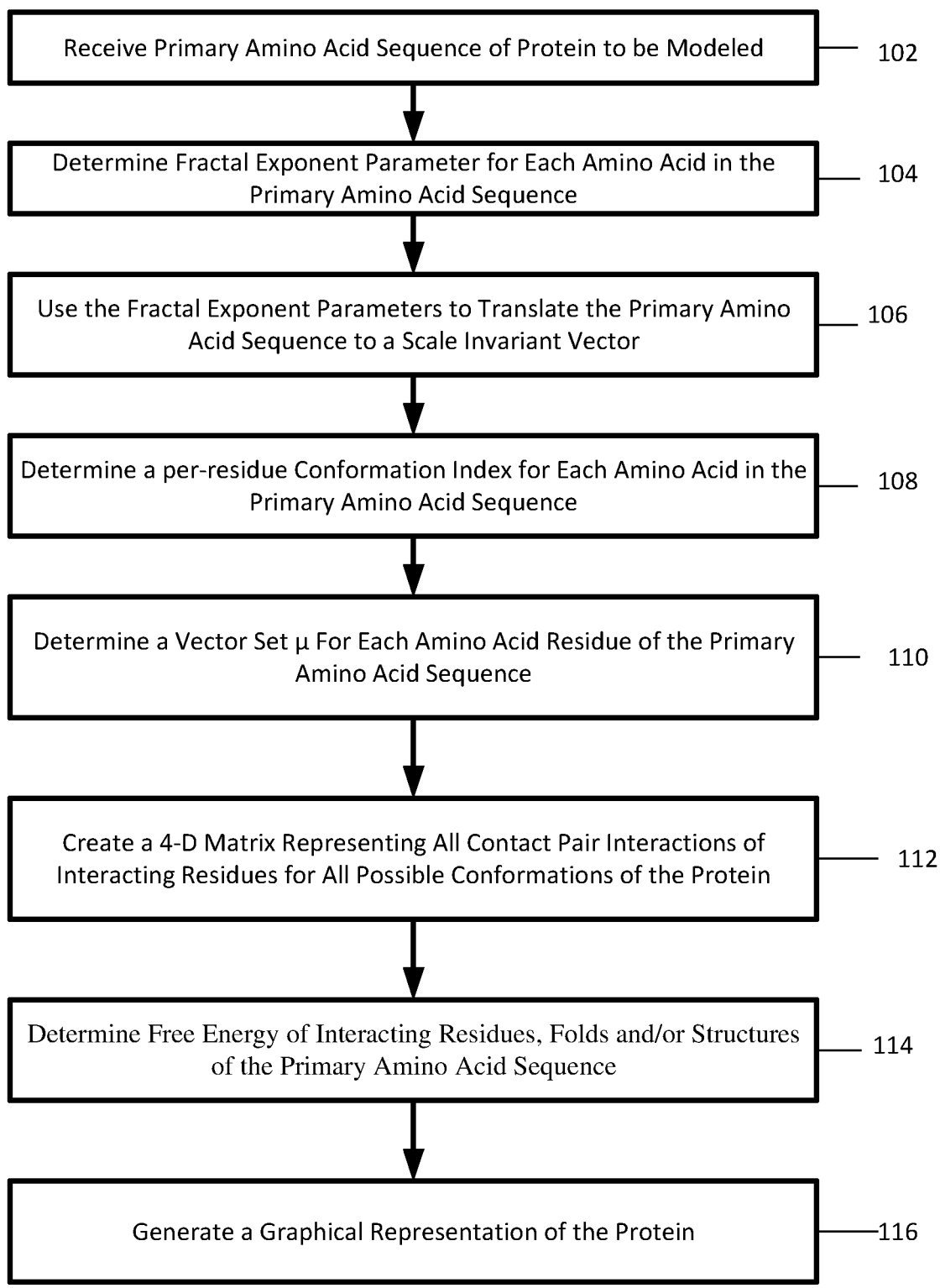
FIG. 1 is a flowchart illustrating an example method for modeling a protein, according to an embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The terms native state, native fold and native conformation as used in this specification refer to the 3-dimensional structure of a folded and functioning protein as determined by its primary amino acid sequence. Many proteins show folding intermediates, which are "non-native" in structure (e.g., compact and partly folded). They are characterized by a reduced amount of tertiary interactions, by a rather large content of secondary structure, and a fluctuating hydrophobic core.

Overview

The current disclosure creates a model that describes proteins in terms of contribution to interaction free energy and allows proteins to be understood both qualitatively and quantitatively without the use of atomistic methods. In an embodiment, the model is based on a per-residue interaction factor or parameter ("μ") that relates to relative stickiness of each residue of a protein structure as it pertains to the organization, fold, and/or function of the protein. Specifically, in an embodiment, thousands of atomic interactions relevant to each residue of a protein are parsed, grouped, and condensed into a reduced, scale-invariant descriptor (i.e., the per-residue interaction factor) for the degrees of freedom of a protein that may then be used to describe one or more protein properties. In an embodiment, the per-residue interaction factor is determined based on two conjectures, the first is related to self-similar statistical properties of proteins and the second is related to propagation of the myriad effects that govern protein compaction. In other words, free energy of a protein is described as a balance between compaction and confinement—a network of μ-weighted (stabilizing) contacts balanced by the entropic penalty of limiting the protein to the specific fold. The per-residue interaction factor, μ, determined using the model of this description captures stabilizing contributions that depend on local protein conformation (σ) and per-residue effects (γ), including such important factors as solvation properties and excluded volume, among other properties, and phase transition-like critical effects via normalization with sharp cut-offs In an embodiment, the per-residue interaction factor may also be utilized in modeling a protein structure to describe protein energetics. For example, the per-residue contribution to compaction can be determined as a function of μ. In an embodiment, the model enables construction of a map of the per-residue contributions to interaction free energy of a protein fold that offers a prima facie understanding of protein behavior and computation of residue-residue interaction free energy from primary sequence data.

Detailed Description

As discussed above, current disclosure creates a model that describes proteins in terms of per-residue contribution to interaction free energy derived using two conjectures. The first conjecture relates to power law exponents derived from the accessible surface area of the protein being modeled. The exponents include fixed contributions (i.e., contributions that do not vary from protein structure to protein structure) to compaction for each amino acid residue which may include, without limitation, the combined impact of solvation, steric/excluded volume, and dispersion; van der Waals interactions; stereoelectronic effects; polar effects; and Coulombic effects. Furthermore, information intrinsic to the amino acid residues in a protein context is included in these exponents. However, the exponents do not contain contributions that vary from protein structure to protein structure, such as, without limitation, temperature, medium effects, or sequence (primary structure context). Moreover, secondary, tertiary, and quaternary structural details, destabilizing charge-charge interactions, and other fine structural details are removed by averaging out of these exponents. Protein backbone and side chain entropy penalty factors may also be absent from these exponents because these do not correlate strongly with side chain accessible surface area.

A model created using the principles described in this disclosure uses these per-residue exponents as reduced complexity descriptors of protein interaction free energy, includes the above effects that are omitted and also builds in the effects of sequence and conformation (discussed below). Hence, the per-residue interaction factor μ is constructed in such a way as to include compaction and confinement contributions that are a function of protein sequence and conformation. In an embodiment, for creating the model amino acid sequence terms (γ) are defined such that they capture the energetic consequences of compaction as it relates to accessible surface area (ASA) but do not capture the confinement penalties. For example, the γ terms may include the combined impact of solvation, steric/excluded volume, stereoelectronics, polar, dispersion, van der Waal's and Coulombic factors for each amino acid residue that are fixed and contribute to compaction. However, contributions from those same factors that change from protein structure to protein structure, variations in temperature and medium effects, sequence and related context dependence, secondary, tertiary, and quaternary structural details, destabilizing charge-charge interactions, and fine structure of back bone (BB) and side chain (SC) conformation may be averaged out. Certain important factors are absent altogether. For instance, primary, secondary, tertiary, quaternary, medium, temperature, back bone and side chain entropy penalties do not correlate with side chain accessible surface area and are not taken into account. As such, the γ terms are specific to amino acids.

The second conjecture relates to the effective contribution of individual residues of the protein being modeled that is described by normalization of a residue's intrinsic contributions with residues nearby in the protein sequence and is dictated by local protein conformation. One simple physical interpretation of this approximation may be, for example, a hypothetical hydration surface centered on the residue of interest. The hydration surface may be defined based on the secondary structural motif in which the residue is observed to participate. Such a normalization simultaneously includes multibody interaction, local structure, and local sequence effects.

In other words, construction of the per-residue interaction factor μ also takes into account the energetic consequences of compaction propagated along the protein length, to some maximum, via residues that share a uniform surface out to an appropriate length. Near the transition from native to non-native states, per-residue interaction factors in a protein can be described as originating from conformation-dependent normalization, which may be a function of, for example, residue identity, residue conformation, local sequence, and propagation length. Secondary, tertiary, and quaternary protein structure reflect the outcome of a constraint optimization of these per-residue interaction factors.

Based on the above two conjectures, a model is developed that describes the protein primary amino acid sequence using the per-residue interaction factor μ and or interaction free energy. The model includes three key features: (1) a high precision scale-invariant (fractal exponent) parameter set for each amino acid type, (2) a simple description of local protein conformation, and (3) normalization of a unique subset of residues for each amino acid in the sequence to determine each amino acid interaction factor.

Referring now to FIG. 1, a flowchart illustrating an example method for modeling a protein parameter (μ) and constructing a potential energy map of a protein fold based on its primary amino acid sequence and per-residue conformation index is shown. While the method 100 is described for the sake of convenience and not with an intent of limiting the disclosure as comprising a series and/or a number of steps, it is to be understood that the process does not need to be performed as a series of steps and/or the steps do not need to be performed in the order shown and described with respect to FIG. 1, but the process may be integrated and/or one or more steps may be performed together, or the steps may be performed in the order disclosed or in an alternate order.

It will be understood that each block of the flowchart illustration in FIG. 1, and combinations of blocks in the flowchart illustration, can be implemented by computer program instructions. These computer program instructions may be provided to a processor or other programmable data processing apparatus to produce a machine, such that the instructions which execute on the processor or other programmable data processing apparatus create means for implementing the functions specified in the flowchart block or blocks. These computer program instructions may also be stored in a computer-readable memory or storage medium that can direct a processor or other programmable data processing apparatus to function in a particular manner, such that the instructions stored in the computer-readable memory or storage medium produce an article of manufacture including instruction means which implement the functions specified in the flowchart block or blocks.

Accordingly, blocks of the flowchart illustration support combinations of means for performing the specified functions, combinations of steps for performing the specified functions and program instruction means for performing the specified functions. It will also be understood that each block of the flowchart illustration, and combinations of blocks in the flowchart illustration, can be implemented by special purpose hardware-based computer systems which perform the specified functions or steps, or by combinations of special purpose hardware and computer instructions.

At 102, the system may receive (or determine) a primary amino acid sequence of a peptide and/or a protein. The particular linear sequence of amino acid residues in a protein defines the primary amino acid sequence, or primary structure, of the protein. The primary structure of a protein may be determined using any now or hereafter known methods.

The system may then retrieve and/or determine 104 a numerical descriptor for each amino acid in the primary amino acid sequence. In an embodiment, the numerical descriptor may be a scale-invariant and/or an exponent parameter ("$\gamma$"). The exponent may be fractal. In an embodiment, the exponent for each amino acid is context and structure independent and is determined based on the accessible surface area. These exponents are fractional and range from approximately $\frac{1}{16}$ (for lysine) to $\frac{1}{4}$ (for cysteine), and are distinctly different for each of the 20 amino acids.

In an embodiment, the system may determine the exponent values using any now of hereafter known methods. For example, the system may determine as follows:

For each amino acid type, $$\text{accessible surface area} \propto N^{-\gamma} \quad (1)$$

Where, $\gamma<1$ at $N>7$ is the length of the peptide segment analyzed.

Furthermore, $$\alpha_r = N^{-\gamma} \quad (2)$$

where $\alpha_r$ is the relative accessible amino acid side chain surface area.

Therefore, the system may determine the $\gamma$ terms for each amino acid if the ASA and/or $\alpha_r$ are known. For example, amino acid propensity scales (hydropathic scales) are known and established by calculating the solvent accessible surface areas for amino acid residues in the expended polypeptide chain or in alpha-helix and multiplying the surface areas by the empirical solvation parameters for the corresponding types of atoms. The system may utilize such scales for deriving the $\gamma$ terms for each amino acid in a sequence of given "N".

Figure 2:
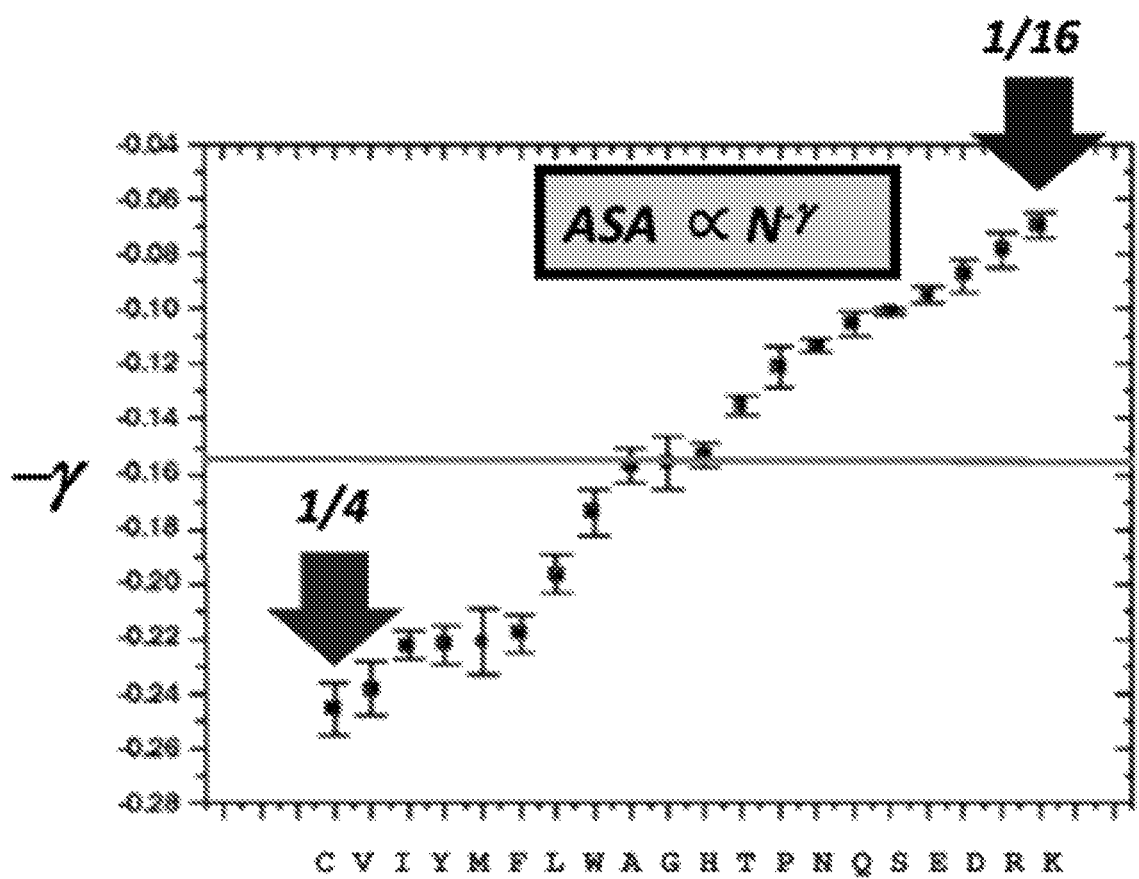
FIG. 2 illustrates a plot illustrating example fractal exponent values for various amino acids, according to an embodiment.

As discussed above, the fractal exponents are small and range from approximately $\frac{1}{16}$ for lysine to $\frac{1}{4}$ for cysteine (FIG. 2). These power laws indicate that amino acid residues—the sequence elements of proteins—exhibit self-similar statistical behavior that bears directly on protein structure. Example exponent values for each amino acid (calculated as discussed above) are listed below in Table 1.

In an embodiment, the system may retrieve the numerical descriptor for the amino acids from, for example, a database that includes the numerical descriptors (e.g., exponent values) for one or more of the 20 amino acids (such as Table 1).

As discussed above, in an embodiment, the exponent values ($\gamma$) are derived from ASA such that they capture the energetic consequences of compaction as it relates to accessible surface area (ASA) but do not capture the confinement penalties, where:

$$G_{(folding)} = \text{compaction} - \text{confinement penalty} \quad (3)$$

TABLE 1

| | |
|---|---|
| A | 0.157 |
| C | 0.246 |
| D | 0.087 |
| E | 0.094 |
| F | 0.218 |
| G | 0.156 |
| H | 0.152 |
| I | 0.222 |
| K | 0.069 |
| L | 0.197 |
| M | 0.221 |
| N | 0.113 |
| P | 0.121 |
| Q | 0.105 |
| R | 0.078 |
| S | 0.101 |
| T | 0.135 |
| V | 0.238 |
| W | 0.174 |
| Y | 0.222 |

At 106, the system may use the numerical descriptors terms (e.g., exponent $\gamma$ values) to translate the primary amino acid sequence $[AA_1, AA_2, AA_3, \ldots AA_N]$ primary amino acid sequence to a first vector $[(B_N) \gamma_1, \gamma_2, \ldots \gamma_{N-1} (B_C) \gamma_N]$, since $\gamma$ is distinctly different for each amino acid. In an embodiment, the first vector may be a scale invariant vector. $B_N$ and $B_C$ are multipliers for terminal residues and may be used if the numerical descriptors correspond to non-terminal amino acid residues.

At 108, the system may then apply symmetry and selection rules to determine a per-residue conformation index ("$\sigma$-index") for each amino acid in the primary amino acid sequence such that the local protein conformation may be classified in terms of the $\sigma$-index. The $\sigma$-index may be used by the system to understand the behavior and properties of a particular fold or conformation in a protein structure. Specifically, the $\sigma$-index describes how solvation drives side chain compaction.

For determining the per-residue conformation index, the system considers proteins at a level of coarseness that removes all molecular fine structure. The σ-index describes the Closest-Linked Nearest Neighbors (clNN) relationship. Specifically clNN are near each other in terms of sequence and have side chains that are separated by less than a solvent molecule. Only one neighbor in each direction of the sequence (N- and C-terminal) can be a candidate for clNN. The clNNs are related by one, two, three, or four steps along the chain and the clNN designation can be σ=1, 2, 3, or 4.

Figure 3:
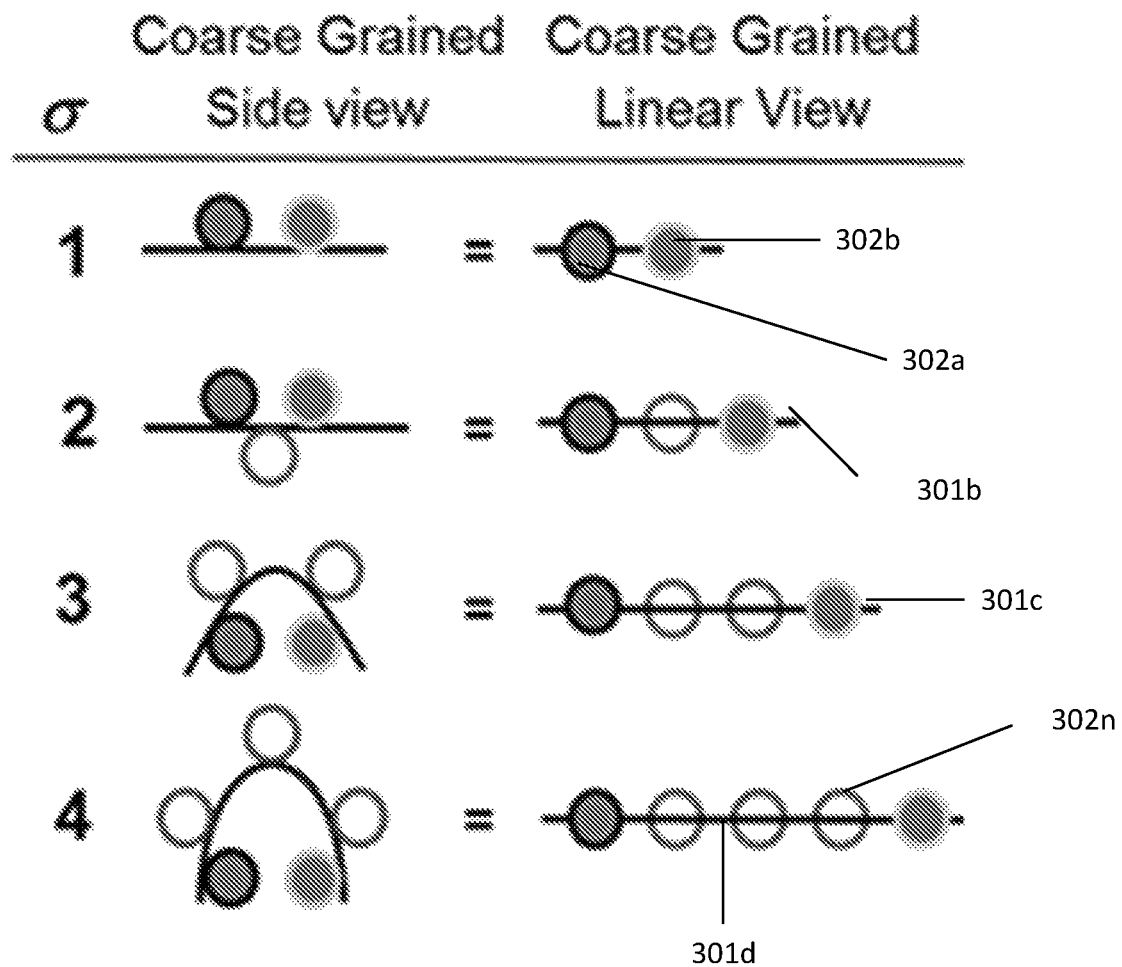
FIG. 3 illustrates the index of the closest-linked nearest neighbor in 2- and 1-dimensional representations for $\sigma=1, 2, 3,$ and $4$, according to an embodiment.

FIG. 3 illustrates index of the clNN in 2-dimensional (coarse grained side view) and 1-dimensional (coarse grained linear view) representation of σ=1, 2, 3, and 4, according to an embodiment. As shown in FIG. 3, for calculation of the σ-index, proteins are considered as flexible chains with identical blobs attached at regular, fixed intervals, and the degree of separation between a residue (grey-filled black circles, e.g., 302a) and the closest linked nearest neighbor (clNN, grey-filled white circle e.g., 302b) defines σ. Proximity of blobs renders them clNN. The closest-linked consideration guarantees that the σ-index refers to residues clustered together whereas the through-space consideration guarantees that the clNN is not simply the next residue in the chain. In this approximation, no reference is made to the atomic structure of a protein, blobs represent the side chains of residues, and the chain represents the protein backbone. The blobs are placed at regular fixed intervals as a consequence of proteins being composed of α-amino acid building blocks identical spacing is a consequence of proteins being composed of α-amino acid building blocks, and proximity of blobs is indicative of the impact of compaction. As shown in FIG. 3, the chain is conveniently represented as a line 301a, 301b, 301c, 301d and blobs as regularly spaced circles 302a-302n. This representation yields a simple notation—a σ-index—that can be used to describe spatial relationships along the backbone in a collectively exhaustive and mutually exclusive way.

In an embodiment, a blob is assigned a σ-index based on the translational relationship, the number of steps within the interval determines the index. An interval can have residues described as clNNs related by one, two, three, or four translational steps (σ-index of 1, 2, 3, 4.). A blob is assigned a σ-index based on the translational relationship within the interval. The closest-linked consideration guarantees that the σ-index refers to blobs that are clustered near each other along the chain. The through-space consideration guarantees that the clNN is not simply the next residue in the chain. Although the clNN definition differs from common definitions of nearest neighbor, it cleanly captures regular secondary structure designations: extended σ=2 intervals correspond to beta strands, repeated σ=3 intervals to the $3_{10}$-helix motif, and repeated σ=4 intervals to the canonical alpha-helix. A such, this index describes canonical secondary motifs in recognizable terms, but also describes loops, turns, and coil structures. For example, a residue that is part of a canonical beta strand would be assigned σ=2, since i+2 and i−2 would be clNN. Were the protein to refold in that region as an extended $3_{10}$ helix the relationships would change to σ=3, since i+3 and i−3 would be the clNN. Importantly, the σ-index descriptor is applicable to all residues in a protein, including both the various turn, extended, and unstructured regions (so called random coil) and the regular repeat regions.

The clNN approach thereby delimits local conformation according to relative amino acid side chain arrangement. This coarse treatment of conformation considers many variations of the local backbone and side chain dihedral angles as soft and energetically equivalent and accommodates small fluctuations.

Figure 4:
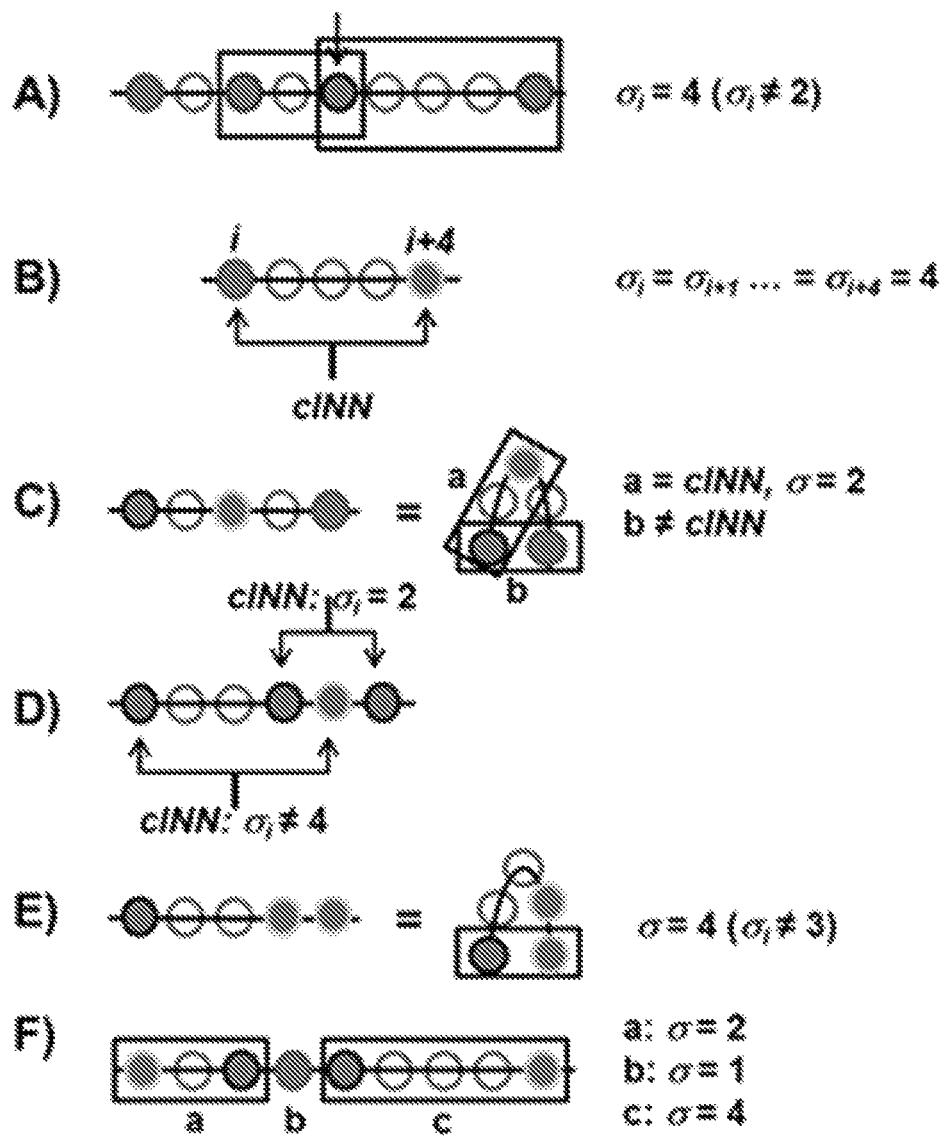
FIG. 4 illustrates example selection rules for determining per-residue conformational index for each amino acid residue, according to an embodiment.

In an embodiment, for assigning the σ-indices, the system may identify the clNN along the chain in both the N and C directions relative to the amino acid of interest (i+/−σ, where σ=1, 2, 3 or 4). Unambiguous per-residue σ-index assignment is then determined using the following selection rules:

(1) Each residue can have only one σ-index (evaluated in both N and C directions)—if the clNN spacing in the N- and C-terminal directions are the same then the clNN is assigned as the σ-index for that amino acid;

(2) IF a single residue has a clNN in the N-direction that is not identical to that of the C-direction the σ-index for that residue is assigned to the larger of the two intervals. In other words, residues at the junction between two different intervals, i.e. a site wherein the N-terminal direction would dictate one σ-index and the C-terminal direction a different σ-index, the residues are assigned the larger σ-index (FIG. 4A);

(3) If no nearest neighbor is identified within the +/−4 residues and the residue falls within the interval of a pair of clNN, the residue is assigned the σ-index of that clNN pair (FIG. 4B);

(4) Two residues that constitute clNNs cannot have a nearest neighbor less that σ residues away in the direction defined by that interval, though they may have a neighbor outside that interval (i.e. more than σ residues away) or in the opposite direction of that interval. In other words, if a clNN is embedded within the interval of another clNN the smaller σ-index takes precedent (FIG. 4C);

(5) If a clNN crosses into an interval of another clNN assignment. The smaller σ-index takes precedent. (FIG. 4D);

(6) As an exception to (5), if i+3 AND i+4 (or i−3 AND i−4) nearest neighbors are identified the clNN is assigned a σ-index of 4 (FIG. 4E); and (7) If the assignment is ambiguous, i.e. cannot be resolved according to the above rules, the residue is assigned a σ-index of 1 (σ=1). (Example: No allowed nearest neighbor identified and the residue does not fall within the interval of another pair of clNNs (FIG. 4F).

The conformational space captured by this model on a per-residue basis is limited to σ=1, 2, 3 and 4, as the σ-index does not appear to exceed σ=4 in canonical proteins. However, other σ-index for, for example, non-canonical molecules are within the scope of this disclosure.

At step 110, the system may determine a vector set for each amino acid residue of the primary amino acid sequence. In an embodiment, the vector set may include values (per-residue interaction factor vector set) for each amino acid in the primary amino acid sequence corresponding to $\sigma_i$ values ($\sigma_i$=1, 2, 3, 4). As discussed above, the energetic consequences of compaction are propagated along the protein length, to some maximum, via residues that share a uniform surface out to an appropriate length. Hence, a reduced descriptor of these consequences (i.e., per-residue interaction factor μ) may be determined to capture this information as a function of relevant residue exponent factor (γ), conformation index (σ), and propagation length (ξ), i.e., μ (γ, σ, ξ).

The determination of the per-residue interaction factor μ is based on the concept that the potential interaction energy of residue i depends on a subset of the nearby residues termed the determinant, or hidden symmetry, set ($\theta_d^i$). A simple relationship pinpoints the hidden symmetry set for residue i of index σ. Specifically, $$i+n\sigma_i \in \theta_d^i, \quad (4)$$

where n=$-\xi_\sigma$, ... -2, -1, 0, 1, 2, ... $\xi_\sigma$, $\xi_\sigma = \lfloor \xi/\sigma \rfloor$, ξ a normalization length. Extensive examination of protein structure supports the use of the same value of ξ (for example, ξ=10) for all proteins and σ-indexes (discussed below). ξ may vary with temperature and medium (pH, etc.), but is typically near 10 at typical biological temperatures and conditions. This long normalization length indicates the critical role of these residues in phase transition-like behavior that governs interaction free energy, for example in the protein folding to unfolding process. For example, ($\theta_d^{117}$ of T4 lysozyme (σ=4; ξ=10; $\xi_\sigma$=2, n=-2, -1, 0, 1, 2) contains five residues ($\theta_d^{117}$=109, 113, 117, 121, 125). Mutation of any of these five residues will impact the interaction factor for residue 117, and hence computed interaction free energies attributable to residue 117, among others. Had this residue been assigned σ=3 then ($\theta_d^{117}$=108, 111, 114, 117, 120, 123, 126. Not all elements of $\theta_d^i$ will necessarily have the same σ-index in the observed protein structure as that assigned to i. This is attributable to the periodic relationship of the set, i.e. the translational symmetry of the blobs defined by a as an extended, if hypothetical, secondary motif. In other words, the set $\theta_d^i$ can be viewed as the extended array of clNNs for i in a hypothetical transient motif that could exist by virtue of protein conformational fluctuations. Whether the other elements of $\theta_d^i$ have the same σ-index as that assigned to i is irrelevant. Returning to the T4 lysozyme example above, the ($\theta_d^{117}$ set for residue 117, which adopts σ=4, is independent of whether residues 109, 113, 121, and 125 actually adopt σ=4 in the native state. Thus, the term hidden and this model may be used to describe certain folding fluctuations as making important contributions.

Hidden symmetry considerations suggest can be viewed as reflective of fluctuation-induced normalization of long range effects such as solvation, excluded volume, or polarity. Equation 5 below is derived to express this idea in mathematical form. Accordingly, for each residue i with index σ, the γ-values (or related variants of γ such as γ+1) of $\theta_d^i$ are summed, normalized, and then assigned as interaction factor $\mu_i^\sigma$ as follows:

$$\mu_i^\sigma = (2\xi_\sigma + 1)^{-1} \sum_{n=-\xi_\sigma}^{\xi_\sigma} \gamma_{i+\sigma n}, \quad \xi_\sigma = \left\lfloor \frac{\xi}{\sigma} \right\rfloor \quad (5)$$

The μ term captures the context- and conformation-dependencies of each amino acid residue in a given fold. In this way, any protein conformation can be deconstructed as being composed of residues of specified σ-indices and the corresponding $\mu_i^\sigma$ terms dictated by the hidden symmetries of these residues. It should be noted that a person skilled in the art would understand that other equations may be used to determine the $\mu_i^\sigma$ terms, for example, by increasing the maximum value of ξ.

Although the exponents are unitless terms derived from relative solvent accessibility, the $\mu_i^\sigma$ term, as discussed below with respect to equation 6, may be related to energy. Accordingly, the $\mu_i^\sigma$ term are sometimes referred to as energies, potentials, or factors, in reference to kT (Boltzmann constant and temperature, or the equivalent), and related expressions as discussed below. Other, more common notions relevant to Equation (5) consist of free boundary condition to assess $\mu_i^\sigma$ for the N- and C-termini., multipliers for the gamma values of the first and last residues of the protein, as needed, where $B_N$=0.45 and $B_C$=0.55 (discussed below). Hence, $\mu_i^\sigma$ can be related to interaction free energy between residue i and residue j (i.e., implicit multi-body interactions).

Figure 5:
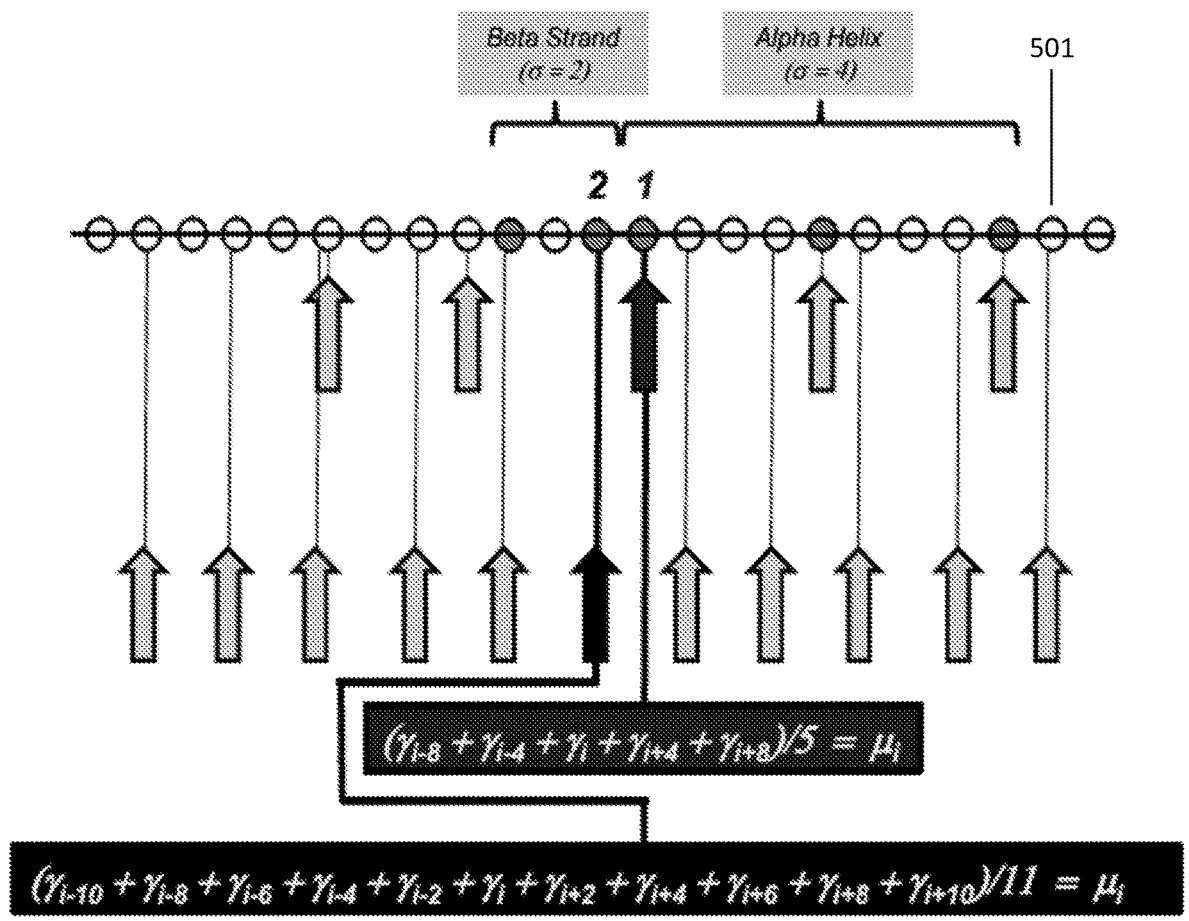
FIG. 5 illustrates an example calculation of the per-residue interaction factor using the method of FIG. 1 for residue 1 ($\sigma=4$) and residue 2 ($\sigma=2$) for an example schematic sequence, according to an embodiment.

FIG. 5 depicts the application of Equation 5 for calculating the $\mu_i$ for residue 1 (σ=4) and residue 2 (σ=2) for the illustrated schematic sequence 501. Using Equation 5, the $\mu_i$ for residue 1 is determined to be: $\mu_i = (\gamma_{i-8} + \gamma_{i-4} + \gamma_i + \gamma_{i+4} + \gamma_{i+8})/5$. The $\mu_i$ for residue 2 is determined to be: $\mu_i = (\gamma_{i-10} + \gamma_{i-8} + \gamma_{i-6} + \gamma_{i-4} + \gamma_{i-2} + \gamma_i + \gamma_{i+2} + \gamma_{i+4} + \gamma_{i+6} + \gamma_{i+8} + \gamma_{i+10})/11$.

At 112, the system may create a multi-dimensional matrix that contains all $\mu_i$ for all possible conformations of the protein (native or otherwise). In other words, the system may determine, for each protein, a matrix: $[[\mu_1, \mu_2 \ldots \mu_N]^{\sigma=1}; [\mu_1, \mu_2 \ldots \mu_N]^{\sigma=2}; [\mu_1, \mu_2 \ldots \mu_N]^{\sigma=3}; [\mu_1, \mu_2 \ldots \mu_N]^{\sigma=4}]$ based on all possible σ-index values for each amino acid residue in the protein. In an embodiment, the multi-dimensional protein may be 4-dimentional (for example, when the σ-index values are 1, 2, 3, and 4). As discussed above, protein structure (secondary, tertiary, and quarternary, etc.) reflects an optimization of the per-residue interaction factors (μ (γ, σ, ξ)). For example, Table 2 below illustrates a 4-dimensional matrix that includes μ values for each residue in a T4 lysozyme protein for each of σ=1, 2, 3, 4. Thus, the resultant matrix includes μ values for any possible conformation for a given amino acid sequence.

At 114, the system may also determine the free energy of interacting residues, folds or structures for the primary amino acid sequence as a function of the per-residue interaction factor μ (γ, σ, ξ). In an embodiment, the free energy of interacting residues i and j is related to the product of the interaction factors, μ, such that $G \sim \varepsilon \tau_{i,j} \mu_i \mu_j$, where G is free energy, ε relates medium effects, and $\tau_{i,j}$ is an interaction efficiency term. The implicit multi-body interactions subsumed in the interaction factors (μ) aim to reflect solvation and other non-local effects that are hidden or obscured by multi-scale correlations.

TABLE 2

| A | B | C | D | E | F | G |
|---|---|---|---|---|---|---|
| 1 | M | 99 | 150 | 155 | 138 | 150 |
| 2 | N | 113 | 150 | 146 | 140 | 95 |
| 3 | I | 222 | 154 | 161 | 171 | 205 |
| 4 | F | 218 | 148 | 136 | 151 | 160 |
| 5 | E | 94 | 152 | 165 | 153 | 91 |
| 6 | M | 221 | 146 | 128 | 125 | 204 |
| 7 | L | 197 | 151 | 172 | 178 | 145 |
| 8 | R | 78 | 155 | 138 | 130 | 113 |
| 9 | I | 222 | 150 | 161 | 167 | 207 |
| 10 | D | 87 | 147 | 133 | 144 | 134 |
| 11 | E | 94 | 147 | 159 | 156 | 109 |
| 12 | G | 156 | 146 | 129 | 122 | 196 |
| 13 | L | 197 | 148 | 164 | 174 | 133 |
| 14 | R | 78 | 148 | 139 | 140 | 116 |
| 15 | L | 197 | 149 | 164 | 143 | 196 |
| 16 | K | 69 | 150 | 132 | 122 | 134 |
| 17 | I | 222 | 151 | 176 | 200 | 121 |
| 18 | Y | 222 | 149 | 126 | 123 | 197 |
| 19 | K | 69 | 155 | 178 | 148 | 128 |
| 20 | D | 87 | 152 | 133 | 138 | 142 |
| 21 | T | 135 | 155 | 172 | 200 | 187 |
| 22 | E | 94 | 160 | 143 | 137 | 137 |
| 23 | G | 156 | 162 | 181 | 159 | 157 |
| 24 | Y | 222 | 159 | 141 | 146 | 193 |
| 25 | Y | 222 | 159 | 169 | 200 | 128 |
| 26 | T | 135 | 154 | 143 | 148 | 155 |
| 27 | I | 222 | 157 | 162 | 134 | 179 |
| 28 | G | 156 | 151 | 146 | 152 | 136 |

TABLE 2-continued

| A | B | C | D | E | F | G |
|---|---|---|---|---|---|---|
| 29 | I | 222 | 150 | 160 | 179 | 138 |
| 30 | G | 156 | 152 | 136 | 124 | 176 |
| 31 | H | 152 | 155 | 168 | 159 | 142 |
| 32 | L | 197 | 156 | 142 | 158 | 148 |
| 33 | L | 197 | 155 | 162 | 184 | 179 |
| 34 | T | 135 | 152 | 143 | 137 | 138 |
| 35 | K | 69 | 146 | 157 | 142 | 140 |
| 36 | S | 100 | 145 | 141 | 133 | 160 |
| 37 | P | 121 | 143 | 144 | 158 | 135 |
| 38 | S | 100 | 135 | 135 | 149 | 133 |
| 39 | L | 197 | 136 | 138 | 115 | 139 |
| 40 | N | 113 | 136 | 141 | 116 | 135 |
| 41 | A | 157 | 136 | 132 | 145 | 133 |
| 42 | A | 157 | 132 | 133 | 162 | 139 |
| 43 | K | 69 | 128 | 129 | 116 | 124 |
| 44 | S | 100 | 130 | 138 | 92 | 121 |
| 45 | E | 94 | 129 | 121 | 128 | 146 |
| 46 | L | 197 | 133 | 140 | 184 | 121 |
| 47 | D | 87 | 140 | 137 | 124 | 134 |
| 48 | K | 69 | 145 | 151 | 103 | 165 |
| 49 | A | 157 | 146 | 138 | 152 | 136 |
| 50 | I | 222 | 140 | 148 | 209 | 139 |
| 51 | G | 156 | 139 | 128 | 112 | 147 |
| 52 | R | 78 | 136 | 146 | 94 | 132 |
| 53 | N | 113 | 136 | 128 | 138 | 130 |
| 54 | C | 246 | 137 | 141 | 196 | 147 |
| 55 | N | 113 | 136 | 128 | 130 | 135 |
| 56 | G | 156 | 141 | 149 | 93 | 125 |
| 57 | V | 238 | 142 | 139 | 133 | 162 |
| 58 | I | 222 | 143 | 142 | 196 | 138 |
| 59 | T | 135 | 145 | 141 | 156 | 129 |
| 60 | K | 69 | 141 | 143 | 102 | 167 |
| 61 | D | 87 | 142 | 148 | 122 | 128 |
| 62 | E | 94 | 139 | 131 | 169 | 131 |
| 63 | A | 157 | 143 | 148 | 172 | 157 |
| 64 | E | 94 | 145 | 138 | 104 | 140 |
| 65 | K | 69 | 144 | 160 | 131 | 137 |
| 66 | L | 197 | 143 | 123 | 151 | 156 |
| 67 | F | 218 | 143 | 163 | 197 | 135 |
| 68 | N | 113 | 142 | 129 | 88 | 137 |
| 69 | Q | 105 | 141 | 160 | 115 | 154 |
| 70 | D | 87 | 138 | 116 | 151 | 131 |
| 71 | V | 238 | 140 | 158 | 210 | 129 |
| 72 | D | 87 | 143 | 124 | 90 | 160 |
| 73 | A | 157 | 142 | 156 | 120 | 141 |
| 74 | A | 157 | 144 | 133 | 164 | 126 |
| 75 | V | 238 | 143 | 148 | 192 | 166 |
| 76 | R | 78 | 145 | 136 | 111 | 138 |
| 77 | G | 156 | 147 | 163 | 120 | 133 |
| 78 | I | 222 | 148 | 138 | 149 | 171 |
| 79 | L | 197 | 146 | 152 | 196 | 138 |
| 80 | R | 78 | 146 | 137 | 132 | 129 |
| 81 | N | 113 | 151 | 160 | 116 | 171 |
| 82 | A | 157 | 144 | 137 | 151 | 154 |
| 83 | K | 69 | 147 | 153 | 188 | 108 |
| 84 | L | 197 | 151 | 151 | 132 | 181 |
| 85 | K | 69 | 148 | 145 | 116 | 165 |
| 86 | P | 121 | 140 | 143 | 168 | 97 |
| 87 | V | 238 | 148 | 146 | 156 | 158 |
| 88 | Y | 222 | 148 | 151 | 132 | 189 |
| 89 | D | 87 | 147 | 150 | 134 | 97 |
| 90 | S | 100 | 148 | 151 | 155 | 154 |
| 91 | L | 197 | 150 | 142 | 156 | 193 |
| 92 | D | 87 | 155 | 164 | 161 | 102 |
| 93 | A | 157 | 159 | 154 | 134 | 170 |
| 94 | V | 238 | 166 | 169 | 167 | 205 |
| 95 | R | 78 | 161 | 157 | 190 | 123 |
| 96 | R | 78 | 169 | 171 | 165 | 157 |
| 97 | C | 246 | 170 | 165 | 142 | 226 |
| 98 | A | 157 | 163 | 169 | 187 | 128 |
| 99 | L | 197 | 159 | 155 | 173 | 136 |
| 100 | I | 222 | 163 | 163 | 140 | 214 |
| 101 | N | 113 | 169 | 169 | 151 | 138 |
| 102 | M | 221 | 167 | 168 | 199 | 156 |
| 103 | V | 238 | 171 | 165 | 181 | 208 |
| 104 | F | 218 | 173 | 180 | 154 | 148 |
| 105 | Q | 105 | 169 | 163 | 151 | 164 |
| 106 | M | 221 | 170 | 169 | 195 | 193 |
| 107 | G | 156 | 171 | 165 | 193 | 153 |
| 108 | E | 94 | 169 | 179 | 161 | 168 |
| 109 | T | 135 | 165 | 150 | 122 | 186 |
| 110 | G | 156 | 166 | 185 | 203 | 141 |
| 114 | F | 218 | 151 | 161 | 179 | 154 |
| 115 | T | 135 | 144 | 135 | 142 | 159 |
| 116 | N | 113 | 148 | 157 | 131 | 120 |
| 117 | S | 100 | 141 | 133 | 133 | 164 |
| 118 | L | 197 | 138 | 145 | 170 | 140 |
| 119 | R | 78 | 141 | 133 | 129 | 111 |
| 120 | M | 221 | 142 | 151 | 131 | 173 |
| 121 | L | 197 | 146 | 143 | 138 | 143 |
| 122 | Q | 105 | 140 | 147 | 170 | 123 |
| 123 | Q | 105 | 142 | 139 | 129 | 155 |
| 124 | K | 69 | 142 | 147 | 122 | 148 |
| 125 | R | 78 | 135 | 131 | 146 | 123 |
| 126 | W | 174 | 134 | 136 | 158 | 134 |
| 127 | D | 87 | 132 | 126 | 115 | 143 |
| 128 | E | 94 | 135 | 142 | 119 | 118 |
| 129 | A | 157 | 137 | 137 | 141 | 145 |
| 130 | A | 157 | 138 | 134 | 153 | 147 |
| 131 | V | 238 | 133 | 139 | 144 | 123 |
| 132 | N | 113 | 130 | 126 | 98 | 128 |
| 133 | L | 197 | 131 | 132 | 123 | 138 |
| 134 | A | 157 | 131 | 127 | 159 | 126 |
| 135 | K | 69 | 131 | 130 | 147 | 129 |
| 136 | S | 100 | 135 | 135 | 107 | 139 |
| 137 | R | 78 | 130 | 129 | 123 | 137 |
| 138 | W | 174 | 130 | 126 | 156 | 114 |
| 139 | Y | 222 | 137 | 143 | 144 | 138 |
| 140 | N | 113 | 140 | 138 | 103 | 157 |
| 141 | Q | 105 | 139 | 141 | 139 | 124 |
| 142 | T | 135 | 134 | 136 | 169 | 135 |
| 143 | P | 121 | 139 | 139 | 123 | 143 |
| 144 | N | 113 | 133 | 133 | 108 | 139 |
| 145 | R | 78 | 132 | 133 | 143 | 118 |
| 146 | A | 157 | 136 | 133 | 153 | 140 |
| 147 | K | 69 | 138 | 139 | 136 | 151 |
| 148 | R | 78 | 142 | 140 | 119 | 123 |
| 149 | V | 238 | 138 | 140 | 155 | 153 |
| 150 | I | 222 | 135 | 138 | 153 | 139 |
| 151 | T | 135 | 140 | 140 | 109 | 114 |
| 152 | T | 135 | 137 | 131 | 128 | 169 |
| 153 | F | 218 | 137 | 144 | 178 | 129 |
| 154 | R | 78 | 138 | 131 | 134 | 110 |
| 155 | T | 135 | 140 | 146 | 107 | 177 |
| 156 | G | 156 | 143 | 133 | 132 | 132 |
| 157 | T | 135 | 142 | 155 | 203 | 117 |
| 158 | W | 174 | 147 | 130 | 128 | 181 |
| 159 | D | 87 | 152 | 167 | 119 | 144 |
| 160 | A | 157 | 146 | 137 | 149 | 126 |
| 161 | Y | 222 | 139 | 155 | 192 | 167 |
| 162 | K | 38 | 140 | 123 | 97 | 125 |

(A: residue number; B: Amino acid identity; C: amino acid gamma value. D-G: computed $\mu$ values where D: $\sigma = 1$; E: $\sigma = 2$; F: $\sigma = 4$; G: $\sigma = 3$).

In an embodiment, $\mu$ enables a simple means by which to compute the energy of interacting residues via a mean field rationale. For the present discussion, possible contributions of charge repulsion may be ignored and the discussion may be limited to residue i and its nearest neighbors j to a maximum of 6. Surface residues with less than 6 neighbors are assigned spectral solvent neighbors. Summation of the energy for each state enables description of the system. For example, association is favored by compaction ($M_f$) and disfavored by confinement ($M_d$). Together these can be used to describe the free energy of association: $F = M_f - M_\mu$. The system then utilizes $\mu_i^o$ to describe the compaction tendencies as pairwise interactions of nearest neighbors i and j ($M_f \sim \Sigma \mu_i^o \mu_j^o$). The $\mu_i^o$ term contains entropic effects that stabilize the structure and originate from solvent, among other effects. The system does not attempt to deconvolute the fine-structure components of $\mu_i^o$ or $M_f$, although this description captures the confinement effect as being opposed by protein backbone entropy ($\Delta S^{bb}$) and sidechain entropy ($\Delta S^{sc}$).

Thus, the free energy of interaction between residues i and j depend on the intrinsic properties of the amino acids ($\gamma$), local conformations ($\sigma$-index), and long-range effects dictated by the hidden symmetries ($\xi$), counterbalanced by the total confinement penalties $\Delta S^{bb}$ and $\Delta S^{sc}$), gives the free energy of a particular fold. Summation over the entire protein of the interactions determined by per-residue factors ($\mu_i^o$) gives the microstate energy of a particular fold F (coarse grain energy). Free energy of a fold, as a function of interaction of residue i with nearest neighbor j may be estimated using the following example equation:

$$\Delta G = \frac{-\lambda \varepsilon}{2} \sum_{i,j\,(i\neq j)}^{n} \tau_{i,j} \mu_i \mu_j - T \sum_{i}^{n} (\Delta S_i^{bb} + \Delta S_i^{sc}) \quad (6)$$

In Equation (6), the sign indicates low energy is favorable; T is temperature in Kelvin; $\gamma$ is a scaling parameter with units of energy; $\varepsilon$ is a medium parameter, $\tau_{ij}$ an efficiency parameter of the i,j-interaction (e.g. polar/non-polar compatibility), and $\Delta S_i^{bb}$ and $\Delta S_i^{sc}$ are protein backbone (bb) and side chain (sc) entropy contributions. In an embodiment, it is assumed that the protein has evolved to an optimum interaction consonance and $\tau$, as well as $\varepsilon$, are set to unity ($\tau=\varepsilon=1$). The first term of Equation (6) captures the net favorable compaction forces between residues i and j captured primarily as $\mu_i^o \mu_j^o$. The second term captures the penalty of limiting the protein backbone and side chain conformational states to enable residues i and j to interact. The change in protein entropy upon confinement depends on the adopted conformation, the amino acid residue, and differences between the non-native and native states. The system utilizes backbone and side chain entropy values determined from evaluation of native and non-native state ensembles to approximate these confinement penalties. The change in protein entropy upon confinement depends on the backbone and sidechain properties in the non-native and native states.

It should be noted that compaction and confinement of a single pair of residues does not take into account long range effects concomitant with mutation of, for example, one of those residues, and therefore the pairwise interactions between the pair of residues i and j cannot be directly applied to protein mutational effects.

It will be understood to those skilled in the art that the free energy of interacting residues is defined by the system as a function of $\mu$ ($\gamma$, $\sigma$, $\xi$), and the relationship may be represented using other equations without deviating from the principles of this disclosure.

It should also be noted that although formally based on two-body interactions, multibody interaction effects are implicit in the $\mu_i^o$ term because of the sequence and local conformation contributions integrated by hidden symmetry considerations. In principle, the model is transferable to any protein and, owing to the simplicity of the factors derived here, is computationally inexpensive. Consider, for example, wild-type and mutant proteins that adopt the same fold and differ only at the site of mutation such that residue X becomes residue Y. The calculated change in free energy of the ground conformational state $\Delta\Delta G_{y-x}$ requires the determination of $\mu_x \rightarrow \mu_y$. Of course, many other $\mu_i^o$ terms will likely change. Therefore, the compaction terms of all residues that contain the mutation site in $\theta_d^i$, must be reevaluated and compared to accurately assess $\Delta\Delta G_{y-x}$. As such, in this model multibody effects dominate the interaction free energy.

As such, the system may model a protein using Equation (5) and/or Equation (6) as a s a function of $\mu$-values, and/or free energy of interacting residues. Hence, the protein modeled using scale-invariant terms; correlated changes are captured in per-residue interaction factors; from these free energy changes may be determined. In Equation (6), the free energy is described as a balance between compaction and confinement—a network of $\mu$-weighted (stabilizing) contacts balanced by the entropic penalty of limiting the protein to the specific fold. The interaction factor, $\mu$, defined in Equation (5), captures stabilizing contributions that depend on local protein conformation ($\sigma$) and per-residue effects ($\gamma$), including such important factors as solvation properties and excluded volume, among other properties, and phase transition-like critical effects via normalization with sharp cutoffs. Although highly simplified, these ideas are in line with the energetic and dynamical properties of proteins being tuned to the energetic and dynamical properties of water, the long range effects of solvation and liquid-vapor coexistence models, and protein-solvent fluctuations across timescales.

Taken together, this model is suggestive of a framework for understanding protein interaction free energy. The model does not attempt to deconvolute free energy in terms of specific atomistic considerations, and provides an anatomy of protein free energy expressed in terms of per-residue contributions (i.e., fractal dimension).

At 116, the system may generate a graphical representation of the protein structure. In an embodiment, the graphical representation may be a plot of $\mu$-values for a given (known) and/or proposed (unknown) structure of an amino acid sequence, a heat-map (also referred to as $\mu$ map, heat map or energy map) for a given (known) and/or proposed (unknown) structure of an amino acid sequence, a tabular format of the 4-D matrix, or some other form of graphical representation that represents the protein structure as a function of $\mu$-values, and/or free energy of interacting residues. In an embodiment, the graphical representation may be displayed to a user, for example, via a display. Alternatively and/or additionally, the graphical display of the protein structure may include one or more user interactive features (e.g., drop down menus for changing one or more values of the parameters for modeling the protein as described above, touch screen or other interactive tabs for changing the position and/or a type of one or more residues in the protein structure, changing the color and/or grey scale value of one or more regions of the graphical display, selecting analytical functions based on the graphical representation, displaying more information corresponding to one or more regions of the graphical display, or the like).

In an embodiment, the graphical representation may be used to validate the given and/or proposed structure (among other applications).

In an embodiment, for generation of the graphical representation (e.g., heat-map) the system may first characterize amino acid residues of a protein ranging on a continuous scale from hot (relatively high $\mu$ values) to cold (relatively low $\mu$ values) as a function of conformation ($\sigma$) and sequence (within 10 or so amino acid residues in the sequence). Alternatively and/or additionally, the system may classify amino acid residues of a protein as either hot or cold by comparing their $\mu$ values to a threshold value (e.g., hot residues will have a $\mu$ value greater than a threshold value and cold residues will have $\mu$ value less than the threshold).

Figure 6:
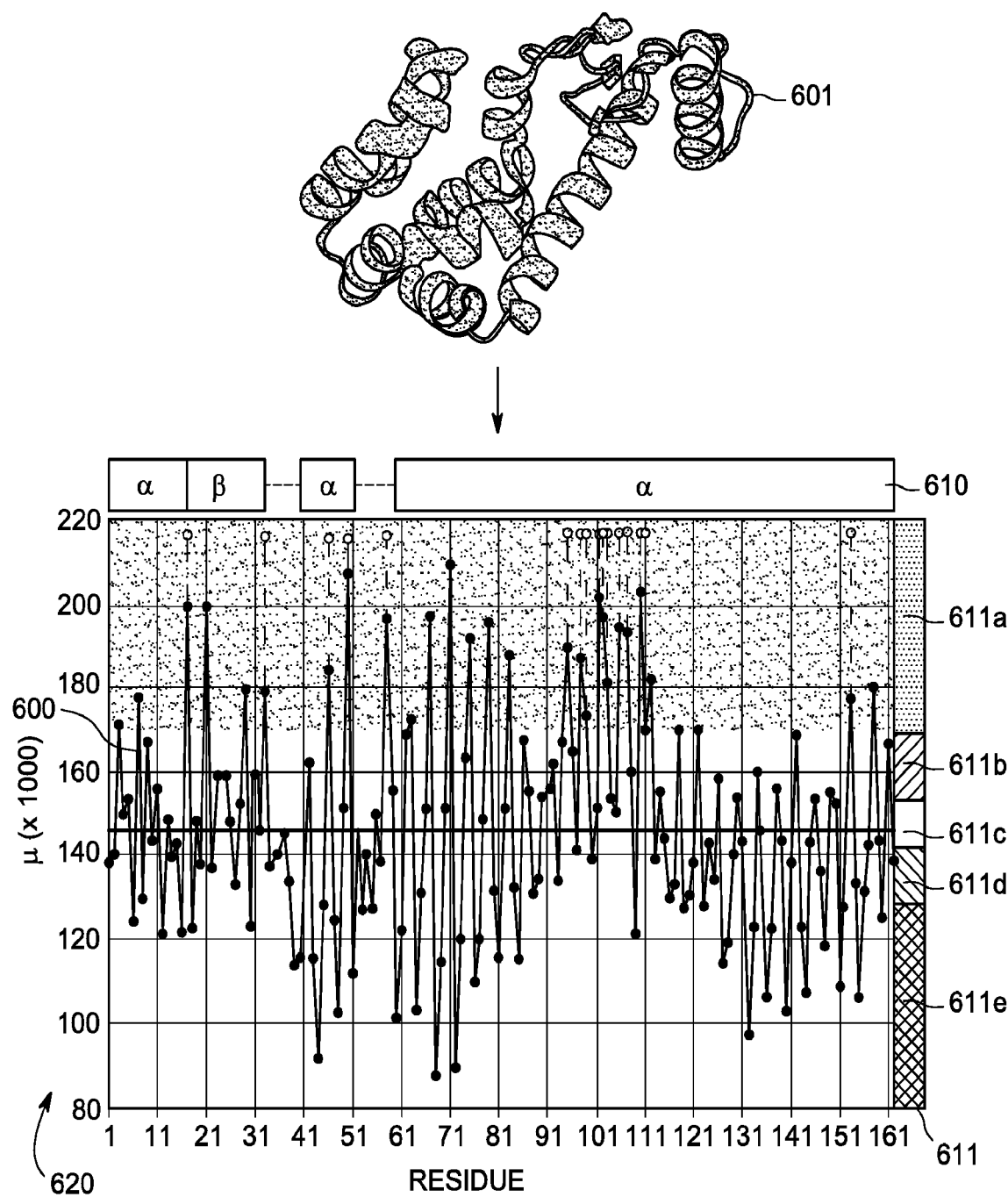
FIG. 6 illustrates an example graphical representation including a plot of µ-values for a known structure of a T4 lysozyme protein, according to an embodiment.

In other words, the contribution of hot residues to the free energy or stability of a protein is higher compared to those of cold residues. Such characterization of the amino acid residues may be represented on a heat-map. Classification into more than two categories are within the scope of this disclosure (e.g., ranging from very hot, less hot, neutral, less cold, very cold in a decreasing level of hotness or μ values as shown in FIG. 6 using different colors and/or grey scale representations). It will be understood to those skilled in the art that the terms hold and cold residues are not limiting, and any other terms may be used to describe and/or represent the differential μ values of a protein on a heat map. Table 3 below illustrates the amino residues of T4L classified into 5 groups:

TABLE 3

| | |
|---|---|
| Very Cold | 6 + 12 + 16 + 18 + 30 + 39 + 40 + 43 + 44 + 47 + 48 + 51 + 60 + 61 + 64 + 68 + 69 + 72 + 73 + 76 + 77 + 81 + 85 + 109 + 127 + 128 + 132 + 133 + 136 + 137 + 140 + 143 + 144 + 148 + 151 + 155 |
| Less Cold | 1 + 2 + 8 + 14 + 20 + 22 + 27 + 34 + 35 + 36 + 38 + 45 + 53 + 54 + 55 + 57 + 65 + 80 + 84 + 88 + 89 + 93 + 100 + 113 + 116 + 117 + 119 + 120 + 121 + 123 + 125 + 141 + 147 + 152 + 154 + 156 + 160 + 162 |
| Neutral | 4 + 10 + 13 + 15 + 19 + 26 + 32 + 37 + 41 + 52 + 56 + 78 + 97 + 115 + 124 + 129 + 131 + 135 + 139 + 145 + 157 + 159 |
| Less Hot | 5 + 11 + 23 + 24 + 25 + 28 + 31 + 42 + 49 + 59 + 66 + 70 + 74 + 82 + 87 + 90 + 91 + 92 + 96 + 101 + 104 + 105 + 108 + 114 + 126 + 130 + 134 + 138 + 146 + 149 + 150 |
| More Hot | 3 + 7 + 9 + 17 + 21 + 29 + 33 + 46 + 50 + 58 + 62 + 63 + 67 + 71 + 75 + 79 + 83 + 86 + 94 + 95 + 98 + 99 + 102 + 103 + 106 + 107 + 110 + 111 + 112 + 118 + 122 + 142 + 153 + 158 + 161 |

FIG. 6 illustrates an example graphical representation including a plot of per-residue μ-factors for the native fold of T4 Lysozyme (T4L). In an embodiment, the given or known structure 601 of T4L (PDB code: 3FA0) is determined using high resolution crystal structure and is used to generate a plot 600. This known structure 601 represents the native ensemble of wild type T4L and many of its mutants. First, for each residue of this 162 amino acid long protein, Equation 5 combined with the appropriate γ exponents (from Table 1) gives the full set of $\mu_i^\sigma$ factors listed above in Table 2. Next, each residue is assigned a σ-index (based on the structure shown in 601) and an appropriate value was each residue is selected from the full set based on the σ-index to generate the matrix shown below in Table 4. The $\mu_i$ values are then plotted against the amino acid residue number to generate the plot 600 for the structure 601. The plot 600 of the computed per-residue μ-factors for the native fold also includes the conventional α-helical and β-sheet motif assignments (610) and a color (or grey scale) gradient (611) to visualize relative μ values of the protein 620, with highest/hottest to lowest/coldest values ranging from very hot 611a, less hot 611b, neutral 611c, less cold 611d, and very cold 611e. The 31 residues with the highest $\mu_i^\sigma$ factors, the 'hottest' residues, are indicated in the top shaded region. In an embodiment, the $\mu_i^\sigma$ factors may be mapped onto the known structure 601 to generate 603.

A structural heat-map of the T4L protein was also generated based on the factors computed as discussed above and is illustrated in FIGS. 7A and 7B. Various colors (and/or gray scale) may be used to indicate high values (hot) and progressively lower values may be colored salmon, white, cyan, and dark blue (cold) in accord with the heat index shown in FIG. 6. Although the heat-map is less exact than the numerical data (FIG. 6), the map facilitates understanding of spatial relationships. As shown in FIGS. 7A and 7B, hot spots dominate the buried interfacial regions, especially the C-terminal domain and to a lesser extent the N-terminal domain. These are indicative of a high degree of stabilization owing to the relation the per-residue factors have to fold energy: $G \sim \mu_i^\circ \mu_j^\circ$. Cold regions dominate exposed surfaces and are comparably less important for stability.

FIGS. 7A and 7B illustrate example heat-maps generated for the native fold of T4L. A heat-map illustrates hot and cold residues of a protein structure and provides a simple way to simultaneously visualize the approximate relative magnitude of interaction factors and protein organization. For example, as shown in FIGS. 7A and 7B, the protein exterior of T4L is dominated by cool residues with the exception of a hot surface of the catalytic/binding site shown in region 701. This is sensible, since these would contribute weakly to interaction free energy. The interior, however, is dominated by hot residues, whose interactions significantly contribute to stability ($G \sim \mu_i \mu_j$). Hence, this model suggests that proteins may be organized such that the interaction factors are optimized. Similarly, canonical hydrophobic amino acid residues i.e. residues with non-polar side chains, tend to be hot, whereas those with polar side chains, especially those with ionic functionality, tend to be cold. Two examples of charged residues with high μ-factors are presented in FIGS. 7C and 7D. Approximately 25% of the residues in each of these classes, however, do not hold to these trends. Thus, the nature of the side-chain without regard for backbone conformation (σ-index) and context is not a reliable predictor of μ factors. For example, leucine, an archetypal nonpolar residue is occasionally cold (L121, L84, L133), even though these residues are fully buried and connected to a hot network of residues. Albeit somewhat solvent exposed, I110 is cold and connected to this same hot network, M120 is cold and highly solvent exposed, and M6 is cold and almost completely surrounded by a separate hot network. Other examples include residue E11, which is solvent exposed, hot, and the key catalytic residue of this enzyme. Residue R96 was the first heat sensitive mutation site discovered and has been studied in detail. Virtually all mutations of this surface exposed residue attenuate thermal stability. Much like E11, R96 is hot and significantly solvent exposed. (shown in FIGS. 7E and 7F).

Figure 7:
FIGS. 7A-7B illustrate an example graphical representations including heat-maps generated for a known structure of a T4 lysozyme protein, according to an embodiment.
FIG. 7C-7F illustrate various regions of the heat-map of FIG. 7A in an enlarged form, according to an embodiment.
Figure 7:
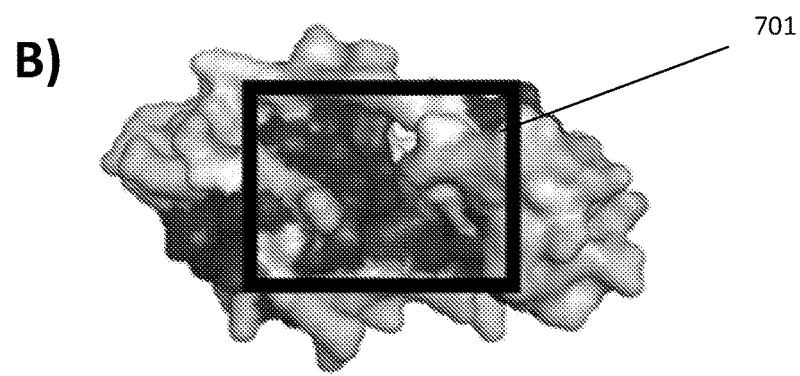
Figure 7:
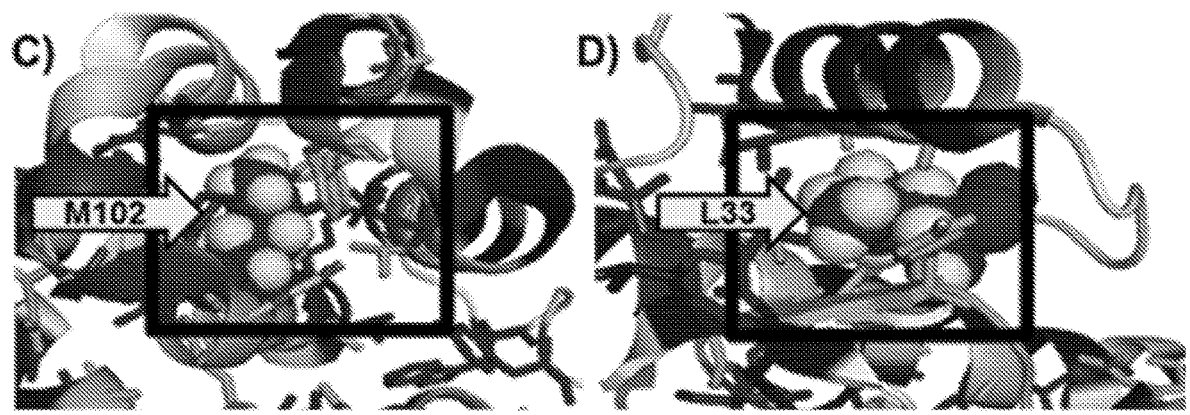

For generation of the heat-map in FIG. 7 above, a σ-index set (based on given and/or proposed native structure) is used as an input for generating a corresponding heat-map by determining the μ values and the multi-dimensional matrix for a given protein conformation. However, it will be understood to those skilled in the art that if the heat-map and amino acid sequence for a protein and/or peptide are known or hypothesized (through homology modeling or computational analysis etc.), the above equations can also be used to generate the σ-index set for the amino acid sequence. Alternatively and/or additionally, if the heat-map and σ-index set for a protein and/or peptide are known or hypothesized, the above equations can also be used to generate (engineer/design) the amino acid sequence for the protein. Similarly, if the if the μ values and/or the σ-index set for a protein and/or peptide are known or hypothesized, the above equations can also be used to generate (engineer/design) the amino acid sequence for the protein.

The above modeling of the structure of a protein and/or peptide to generate an energy may makes it possible to describe protein energetics exactly without resorting to all-atom modeling. In an embodiment, the heat-map may be used to analyze and describe protein energetics, of residue pockets, buried/exposed surfaces, and/or exposed protein surfaces. It does not require high computing power and can be performed on common laptop computers in real time. It will be understood to those skilled in the art that many of the assumptions presented above were a matter of convenience, and more elaborate models based on these ideas may be created using similar principles to further improve exactness. The above method enables visualization of protein behavior, qualitative understanding of protein behavior without resorting to complex numerical analysis, and quantitative determination of protein behavior via easy to perform and reliably accurate methods. Furthermore, it allows for successful conversion of sequence space—which flourishes at the present time due to the genomic revolution—to energy space and suggests that the statistical approaches used to navigate genomic data can be converted into energy signatures and that a transition from correlation to causation may be possible.

TABLE 4

| Ranges | Low | High |
|---|---|---|
| Very Hot (611a in FIG. 6) | 166 | |
| Less Hot (611b in FIG. 6) | 151 | 165,9999 |
| Neutral (611c in FIG. 6) | 141 | 150,9999 |
| Less Cold (611d in FIG. 6) | 126 | 140,9999 |
| Very Cold (611e in FIG. 6) | | 125,9999 |

| Residue | AA | $\mu \times 10^3$ | $\sigma$ | Ranges |
|---|---|---|---|---|
| 1 | M | 138 | A | Cold |
| 2 | N | 140 | A | Cold |
| 3 | I | 171 | A | Very Hot |
| 4 | F | 151 | A | Neutral |
| 5 | E | 153 | A | Hot |
| 6 | M | 125 | A | Very Cold |
| 7 | L | 178 | A | Very Hot |
| 8 | R | 130 | A | Cold |
| 9 | I | 167 | A | Very Hot |
| 10 | D | 144 | A | Neutral |
| 11 | E | 156 | A | Hot |
| 12 | G | 122 | A | Very Cold |
| 13 | L | 148 | R | Neutral |
| 14 | R | 140 | A | Cold |
| 15 | L | 143 | A | Neutral |
| 16 | K | 122 | A | Very Cold |
| 17 | I | 200 | A | Very Hot |
| 18 | Y | 123 | A | Very Cold |
| 19 | K | 148 | A | Neutral |
| 20 | D | 138 | A | Cold |
| 21 | T | 200 | A | Very Hot |
| 22 | E | 137 | A | Cold |
| 23 | G | 159 | A | Hot |
| 24 | Y | 159 | R | Hot |
| 25 | Y | 159 | R | Hot |
| 26 | T | 148 | A | Neutral |
| 27 | I | 134 | A | Cold |
| 28 | G | 152 | A | Hot |
| 29 | I | 179 | A | Very Hot |
| 30 | G | 124 | A | Very Cold |
| 31 | H | 159 | A | Hot |
| 32 | L | 148 | B | Neutral |
| 33 | L | 179 | B | Very Hot |
| 34 | T | 138 | B | Cold |
| 35 | K | 140 | B | Cold |
| 36 | S | 141 | B | Cold |
| 37 | P | 144 | B | Neutral |
| 38 | S | 135 | B | Cold |
| 39 | L | 115 | A | Very Cold |
| 40 | N | 116 | A | Very Cold |
| 41 | A | 145 | A | Neutral |
| 43 | K | 116 | A | Very Cold |
| 44 | S | 92 | A | Very Cold |
| 45 | E | 128 | A | Cold |
| 46 | L | 184 | A | Very Hot |
| 47 | D | 124 | A | Very Cold |

TABLE 4-continued

| 48 | K | 103 | A | Very Cold |
|---|---|---|---|---|
| 49 | A | 152 | A | |
| 50 | I | 209 | A | Very Hot |
| 51 | G | 112 | A | Very Cold |
| 52 | R | 146 | B | Neutral |
| 53 | N | 128 | B | Cold |
| 54 | C | 141 | B | Cold |
| 55 | N | 128 | B | Cold |
| 56 | G | 149 | B | Neutral |
| 57 | V | 139 | B | Cold |
| 58 | I | 196 | A | Very Hot |
| 59 | T | 156 | A | Hot |
| 60 | K | 102 | A | Very Cold |
| 61 | D | 122 | A | Very Cold |
| 62 | E | 169 | A | Very Hot |
| 63 | A | 172 | A | Very Hot |
| 64 | E | 104 | A | Very Cold |
| 65 | K | 131 | A | Cold |
| 66 | L | 151 | A | Neutral |
| 67 | F | 197 | A | Very Hot |
| 68 | N | 88 | A | Very Cold |
| 69 | Q | 115 | A | Very Cold |
| 70 | D | 151 | A | Neutral |
| 71 | V | 210 | A | Very Hot |
| 72 | D | 90 | A | Very Cold |
| 73 | A | 120 | A | Very Cold |
| 74 | A | 164 | A | Hot |
| 75 | V | 192 | A | Very Hot |
| 76 | R | 111 | A | Very Cold |
| 77 | G | 120 | A | Very Cold |
| 78 | I | 149 | A | Neutral |
| 79 | L | 196 | A | Very Hot |
| 80 | R | 132 | A | Cold |
| 81 | N | 116 | A | Very Cold |
| 82 | A | 151 | A | Neutral |
| 83 | K | 188 | A | Very Hot |
| 84 | L | 132 | A | Cold |
| 85 | K | 116 | A | Very Cold |
| 86 | P | 168 | A | Very Hot |
| 87 | V | 156 | A | Hot |
| 88 | Y | 132 | A | Cold |
| 89 | D | 134 | A | Cold |
| 90 | S | 155 | A | Hot |
| 91 | L | 156 | A | Hot |
| 92 | D | 161 | A | Hot |
| 93 | A | 134 | A | Cold |
| 94 | V | 167 | A | Very Hot |
| 95 | R | 190 | A | Very Hot |
| 97 | C | 142 | A | Neutral |
| 98 | A | 187 | A | Very Hot |
| 99 | L | 173 | A | Very Hot |
| 100 | I | 140 | A | Cold |
| 101 | N | 151 | A | Neutral |
| 102 | M | 199 | A | Very Hot |
| 103 | V | 181 | A | Very Hot |
| 104 | F | 154 | A | Hot |
| 105 | Q | 151 | A | Neutral |
| 106 | M | 195 | A | Very Hot |
| 107 | G | 193 | A | Very Hot |
| 108 | F | 161 | A | Hot |
| 109 | T | 122 | A | Very Cold |
| 110 | G | 203 | A | Very Hot |
| 111 | V | 171 | B | Very Hot |
| 112 | A | 183 | B | Very Hot |
| 113 | G | 140 | B | Cold |
| 114 | F | 154 | B | Hot |
| 115 | T | 144 | R | Neutral |
| 116 | N | 131 | A | Cold |
| 117 | S | 133 | A | Cold |
| 118 | L | 170 | A | Very Hot |
| 119 | R | 129 | A | Cold |
| 120 | M | 131 | A | Cold |
| 121 | L | 138 | A | Cold |
| 122 | Q | 170 | A | Very Hot |
| 123 | Q | 129 | A | Cold |
| 124 | K | 142 | R | Neutral |
| 125 | R | 135 | R | Cold |
| 126 | W | 158 | A | Hot |
| 127 | D | 115 | A | Very Cold |
| 128 | E | 119 | A | Very Cold |

TABLE 4-continued

| | | | | |
|---|---|---|---|---|
| 129 | A | 141 | A | Cold |
| 130 | A | 153 | A | Hot |
| 131 | V | 144 | A | Neutral |
| 132 | N | 98 | A | Cold |
| 133 | L | 123 | A | Cold |
| 134 | A | 159 | A | Hot |
| 135 | K | 147 | A | Neutral |
| 136 | S | 107 | A | Very Cold |
| 137 | R | 123 | A | Very Cold |
| 138 | W | 156 | A | Hot |
| 139 | Y | 144 | A | Neutral |
| 140 | N | 103 | A | Very Cold |
| 141 | Q | 139 | A | Cold |
| 142 | T | 169 | A | Very Hot |
| 143 | P | 123 | A | Very Cold |
| 144 | N | 108 | A | Very Cold |
| 145 | R | 143 | A | Neutral |
| 146 | A | 153 | A | Hot |
| 147 | K | 136 | A | Cold |
| 148 | R | 119 | A | Very Cold |
| 149 | V | 155 | A | Hot |
| 150 | I | 153 | A | Hot |
| 151 | T | 109 | A | Very Cold |
| 152 | T | 128 | A | Cold |
| 153 | F | 178 | A | Very Hot |
| 154 | R | 134 | A | Cold |
| 155 | T | 107 | A | Very Cold |
| 156 | G | 132 | A | Cold |
| 157 | T | 142 | R | Neutral |
| 158 | W | 181 | B | Very Hot |
| 159 | D | 144 | B | Neutral |
| 160 | A | 126 | B | Cold |
| 161 | Y | 167 | B | Very Hot |
| 162 | K | 140 | R | Cold |

In an embodiment, the system may be configured to use the model (using Equation 5 or Equation 6), the generated plot of FIG. the heat-map of FIG. 7, and/or other graphical representations of the protein for various application, such as, for example and without limitation, assessing stability of a protein structure; design of antibody drug conjugates (modified proteins, linkers, peptides, etc.); determination of cyclic and linear peptide and protein structure, be it natural or unnatural, based on sequence (and related alternatives as indicated in previous slide); determination of folding mechanism of a protein (non-folded to folded form); analysis of dynamics, i.e., fluctuations within or between folds with or without external factors); design of conformational switches (variable conformational states of contextual structure); design of mutants to modify protein stability, to create, remove, modify or attenuate surface hot spots, enhance solubility, crystallinity, aggregation properties; design and post-translational modifications (dependence of a fold, hot spots, etc., on AA variants); design and modification of catalysis (bond breaking/forming reactions); identification, modulation, attenuation of protein-protein interactions—including antibody or antibody-like (protein/peptide) to antigen (protein/peptide/small molecule/target surface/material); identification, modulation, attenuation of protein-small molecule interactions—including antibody or antibody-like (protein/peptide) to target (ligands, fragments, drugs, drug candidates, diagnostics, therapeutics, tool compounds); identification, modulation, attenuation of protein-bio-macromolecule interactions—same as above to small or large RNA or DNA fragments, designed or natural, including chimeric variant constructs (e.g. peptide/RNA, or peptide-linked nucleobase, etc.); identification, modulation, attenuation of protein-medium interactions/dependence (solvent, temperature, membranes); design of peptide/proteins given sequence or conformation or target; design of small or large molecules (including peptide and protein) that have selectivity over isoforms, mutants, and related targets; description, understanding, and design of biologic target surfaces (including masked or otherwise hidden target surfaces and variations from species to species); design of biologics (humanization of non-human antibodies or antibody equivalents); conversion of bioinformatics data (amino acid sequence) to bio(energetic) informatics; or the like.

In an embodiment, the model of this disclosure may be used to identify and engineer molecules (e.g. protein, peptide, small or drug-like molecules) that bind to a specific region of a protein (binding pocket, surface, antibody, enzyme, kinase, signaling protein, etc.). For example, potential binding sites may be composed of hot and cold residues and molecules may be engineered such that upon binding they interact with hot residues. Such engineered molecules would be superior to those molecules that, upon binding, interact with cool residues.

For example, a heat map generated using the method of FIG. 1 may be used to design molecules that bind to a specific targeted kinase. Since kinases adopt different conformations (sometimes termed 'in' and 'out') the heat maps of each conformation may be analyzed. A closely related example is the use of multiple heat maps to design molecules that selectively bind one target over others. For example, kinase selectivity is viewed as perhaps the central challenge to kinase inhibitor development. Heat maps of multiple kinases (and, if relevant, each conformation) can be used to engineer molecules that will bind selectively to one kinase over the others by targeting unique combinations of residues in a combined positive/negative design strategy.

In yet another embodiment, the model of this disclosure may be used to design peptides to be "hot" in certain conformations such that they bind a protein or small molecule target. For example, the model may be used to map and engineer peptide:MHC binding (MHC: major histocompatibility complex), an interaction which is not only essential to immunity and immune-related diseases such as diabetes, but can also play a role in cancer treatment. Another example would be the use of heat maps to design peptides to bind to antibodies with binding desired affinity. Such peptides may be used, for example, for the identification of autoantibodies in early disease detection or for the inhibition of autoantibodies in autoimmune diseases.

In another embodiment, methods contemplated by the instant application can be utilized to generate heat maps of proteins composed of the non-canonical amino acids. Such non-canonical amino acids can include, but are not limited to, post-translationally modified amino acids such as phosphor-tyrosine, protonated glutamic acid, reduced and oxidized forms of cysteine, ubiquitinated lysine.

In an embodiment, σ, γ, and μ values for new and variant forms of amino acids can be estimated based on the exact values determined for the canonical 20 amino acids. As a non-limiting example, tyrosine phosphorylation is critical in many protein signaling and binding processes and impacts conformational energetics. While tyrosine itself has a high gamma value, this value is significantly reduced when tyrosine is converted to its non-canonical form, anionic phosphotyrosine. Similarly, glutamic acid has a low gamma value because in the canonical form it is an anion as well. The protonated form of this amino acid is important for catalysis and in other instances and can be estimated to be similar to glutamine. The oxidized form of cysteine has a relatively high gamma value, whereas the reduced is predicted to have a lower gamma value. An example for an amino acid with a very low gamma value is lysine. Conversion of lysine to N-acetyl and related structures and/or the ubiquination of the amino acid are predicted to significantly increase the gamma value of the resulting structure. Such changes in gamma value can also be estimated based on the many other amino acids that contain amide functionality, such as glutamine and asparagine.

In another embodiment, methods contemplated by the instant disclosure can be utilized to aid protein visualization. Molecular visualization software such as PyMOL can be used to highlight different regions of a protein in different colors. For instance, residues associated with sigma, gamma, and/or mu values above a certain fixed or user-defined thresholds may be labeled in a specific color to indicate 'hot'. Residues associated with sigma, gamma, and/or mu values below this threshold may be highlighted in a different color, allowing for a color-coded protein image that can be readily interpreted and aide in the identification and modulation of protein-protein-interactions.

In another embodiment, methods described in this disclosure may be used to model proteome and/or structure databases, and analysis of the models of such proteomes and structural protein databases can be used to gain insights into protein properties (e.g., important protein interaction networks, protein signaling pathways, protein drug-target identification, and protein inhibitor, reagent, or drug development). Furthermore, the proteomes of organisms/viruses can be evaluated, unique sequences can be identified, real or hypothetical structures can be modeled, mutants can be evaluated, surface hot spots can be mapped, binding can be rationalized and binding inhibitors designed, among others. Similarly, databases, such as protein structure databases (experimentally determined or hypothetical 3-dimensional models) can also be analyzed using the modeling approach described herein. For example, the 273 proteins (32,767 amino acids) of T4 bacteriophage proteome can be evaluated easily (full heat-map may be generation within a computation time<5 minutes). In addition, unique sequences can be identified (e.g. the serine in the sequence FTNSLRM is unique in the T4 bacteriophage proteome and its mu values depend on the amino acid context and fold), mutants rationalized (the serine in this sequence corresponds to S117, which is helical and in the T4 lysozyme protein; mutation of S117V is the most stabilizing non-cysteine single mutant known for this protein), binding hot spots can be mapped (e.g. FIG. 7D). The derived information may then be used to rationalize, design, or engineer proteins, variants, binding partners, etc.

In an embodiment, the above models and results of analysis (e.g., the matrix including µ values, the free energy model, the µ value plot, the heat-map and/or further applications of the models may be displayed to a user, via for example a display device.

Figure 8:
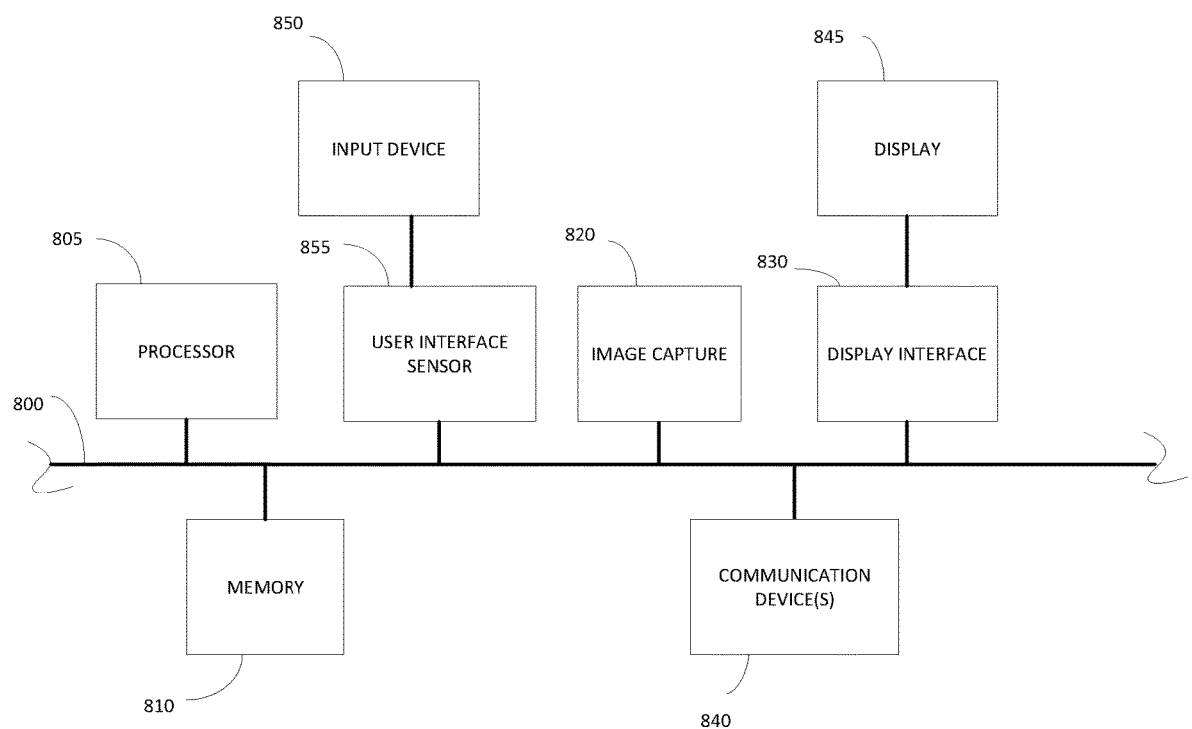
FIG. 8 illustrates an exemplary processing system for performing one or more steps of the method of FIG. 1, according to an embodiment.

FIG. 8 is a block diagram illustrating internal hardware of a processing system 800 adapted for performing the process 100 discussed above. The system 800 is based upon a suitably configured processing system adapted to implement the exemplary embodiment of the present disclosure. Any suitably configured processing system is similarly able to be used as the processing system 800 by embodiments of the present disclosure, for example, a personal computer, workstation, or the like.

The hardware may be used to contain or implement program instructions, such as those of a cloud-based server, electronic device, virtual machine, or container. An electrical bus 800 serves as an information highway interconnecting the other illustrated components of the hardware. Processor 805 is a central processing device of the system, configured to perform calculations and logic operations required to execute programming instructions. As used in this document and in the claims, the terms "processor" and "processing device" may refer to a single processor or any number of processors in a set of processors. Read only memory (ROM), random access memory (RAM), flash memory, hard drives and other devices capable of storing electronic data constitute examples of memory devices 810. A memory device may include a single device or a collection of devices across which data and/or instructions are stored.

An optional display interface 830 may permit information from the bus 800 to be displayed on a display device 845 in visual, graphic or alphanumeric format. An audio interface and audio output (such as a speaker) also may be provided. Communication with external devices may occur using various communication devices 840 such as a transmitter, transceiver, antenna, communications port or a similar device. A communication device 840 may be attached to a communications network, such as the Internet, a local area network or a cellular telephone data network.

The hardware may also include a user interface sensor 855 that allows for receipt of data from input devices 850 such as a keyboard, a mouse, a joystick, a touchscreen, a remote control, a pointing device, a video input device and/or an audio input device. Data also may be received from an image capturing device 820, such of that a scanner or camera.

The following examples are given by way of illustration of the present invention and should not be construed to limit the scope of the present invention.

Example 1

Identification of Hot and Cold Regions

In an embodiment, the system may use the model and the heat-map to identify—within the protein interior—hot and cold regions. These would typically correspond to rigid regions (dominated by clusters of relatively hot residues) and flexible regions (clusters of relatively cool residues) of the protein. For example, the 31 residues of T4L with the highest µ factors, i.e. the 'hottest' residues, are indicated in the top shaded region of FIG. 6. The two largest hot clusters constitute the C- and N-terminal domain cores (FIGS. 7D and 7E, respectively). The N-terminal domain, which is known to be the less stable of the two, has a smaller core, and has significantly fewer hot residues in the core than the C-terminal domain. An uninterrupted vein of hot residues connect the two domains. All of the 31 hottest residues, except for Q122 and W158, make extensive contacts with other hot residues, and 23 of the 31 hottest residues co-localize in four clusters. Although the clustering leads to the protein interior being dominated by hot (sticky) residues and the exterior being dominated by cool (not as sticky) residues, there are some cool residues that are buried and some hot residues that are on the protein surface.

In an embodiment, the system may also use the model and the heat-map to identify hot and cold regions on the protein surface. These would typically correspond to binding regions (i.e. 'sticky' regions dominated by clusters of relatively hot surface residues) and non-binding regions (i.e. less 'sticky' regions dominated by clusters of relatively cool surface residues) with respect to binding/catalytic sites. For example, the most noticeable hot spot on the protein surface is the swath of contiguous hot residues that constitute the substrate binding region (FIG. 7B).

Example 2

Hot Residue Cluster Analysis

Figure 9:
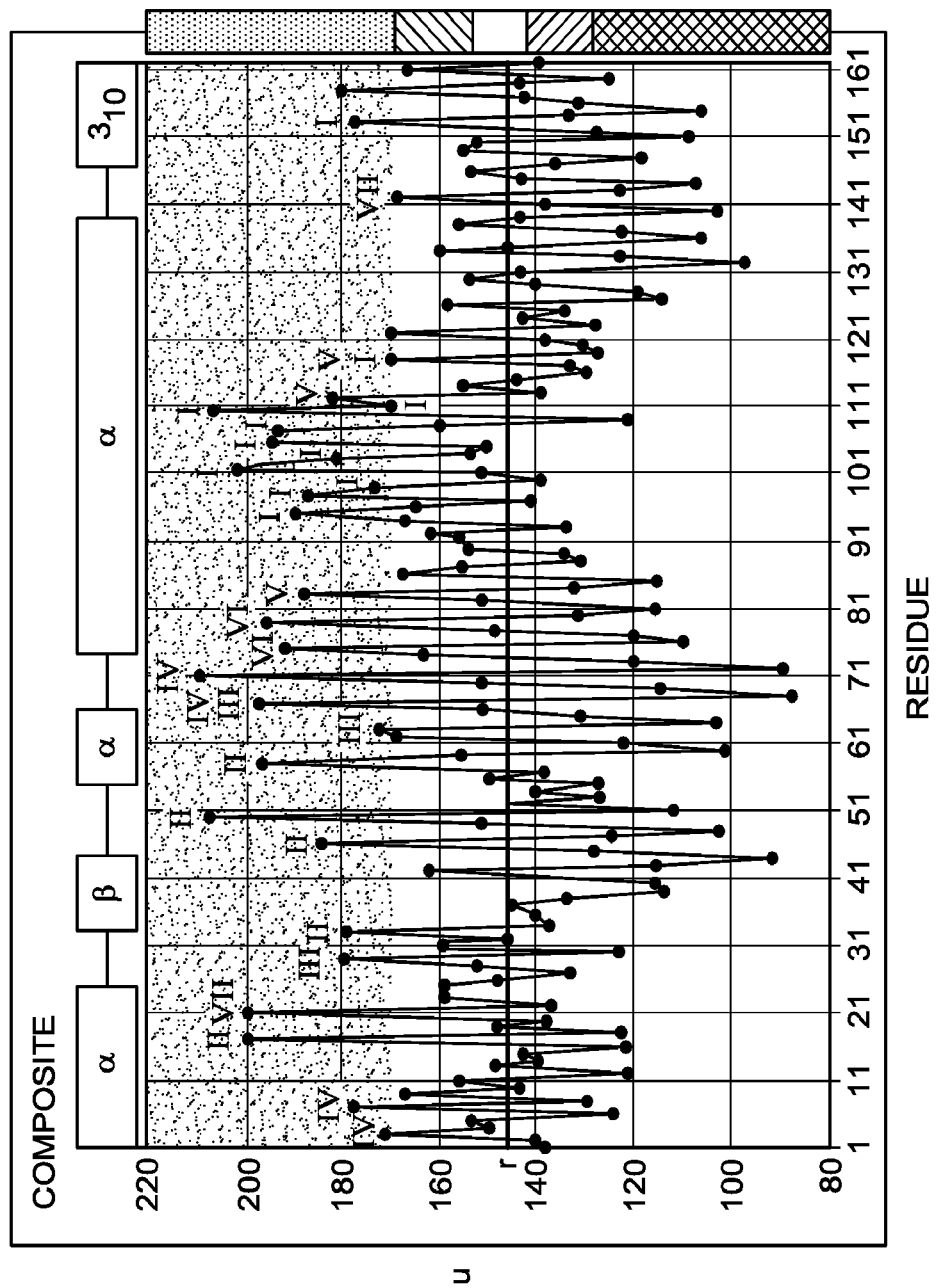
FIG. 9 illustrates the plot of FIG. 6 identifying various hot residue clusters, according to an embodiment.

In an embodiment, the system may use the plot of FIG. 6 for hot residue cluster analysis. Example relative clustering of the hottest 31 residues in the T4 lysozyme is shown in FIG. 9. Hot residues have the potential to contribute most to native state stabilization, and this set forms the hottest clusters, as labeled in FIG. 9 (I-VII). The two largest hot networks constitute the C- and N-terminal domain cores. The C-domain core residues are 95, 98, 99, 102, 103, 106, 111, 118, 153 (I). Residues 107 and 110 are also included because these are solvent exposed. The N-terminal domain core has many fewer residues, specifically 17, 33, 46, 50, and 58 (II). The other hottest residues not part of these cores also cluster together, including residues 29, 63, and 67 (III), 3, 7, 67, and 71 (IV), the small cluster that shares residue 118 with the C-domain core but lacks contacts with the other core residues (83, 112 and 118, V), the small cluster 75, 79 (VI), and the isolated contact pair 21 and 142 (VII). Only two of the hottest residues (122 and 158) do not cluster with the other 29, though the two are still clustered with other hot residues. Remarkably, the 23 of the 31 hottest residues are organized in only four clusters and form extensive contact networks with each other. The remaining 7 residues also make contacts with some of these and other hot residues. This trend continues for progressively cooler residues as well.

Example 3

Protein Stability and Mutant Analysis

In an embodiment, the system may utilize the above model and/or the heat-map to analyze the impact of mutations on the thermal stability of a protein fold.

One important area in which the protein structure modeling discussed above with respect to FIG. 1 could be useful is in engineering proteins of enhanced stability. Biologics, enzymes, and biomaterials depend on protein stability (thermal) for proper function, and certain commercial protein products benefit from increased thermal stability. Single-site mutagenesis offers a means by which to achieve enhanced stability, but without guidance provided by an understanding of protein energetics the process is largely empirical and labor intensive. The above model and heat-map can helpful in understanding the temperature-sensitive mutants of the well-studied T4 bacteriophage lysozyme protein both qualitatively and quantitatively.

The energy gap between the native ensemble and the non-native ensemble largely determines protein thermal stability. A decrease in thermal stability of a mutant relative to wild type protein corresponds to a positive change in free energy ($\Delta\Delta G > 0$) and reflects either destabilization of the native state or stabilization of the non-native states. The converse holds as well, i.e. in isolation, the experimental measure of thermal stability ($\Delta\Delta G_{exp}$) does not reveal which state or states mutation perturbs. Theoretical appraisal does not require a priori knowledge of which states are perturbed provided the energetics of a suitably representative set of microstates are computed accurately, but this task is both difficult to achieve and difficult to know with certainty that it has been achieved. The problem is traceable to the potentially large number of folds that need to be assessed for each protein/mutant pair and the limitation that high resolution structural data is available essentially only for the native state. The alternative, determination of mutational effects based on analysis of the native state alone, remains particularly challenging. Knowledge of whether the mutation primarily impacts the native state is required—without it mutational analysis risks irrelevance with it native state analysis becomes profoundly insightful.

The model of this disclosure model enables speculation regarding ground state analysis. Accordingly, the system may use the model to identify mutations that are expected to primarily impact the ground state, and then determine the corresponding change in thermal stability ($ddG_{calc}$) of these mutants based on evaluation of the native state alone.

Figure 10:
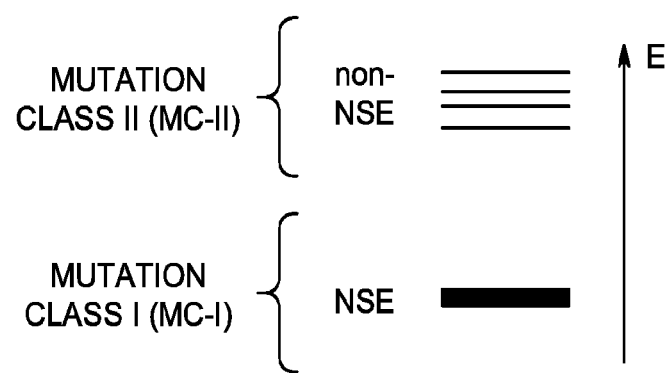
FIG. 10 illustrates the classification of various mutations to a protein structure based on whether the impact of mutation is expected to be primarily on the native state ensemble (NSE) or on the non-native state ensemble (non-NSE), according to an embodiment.

For example, the model can be used to categorize the impact of mutation on thermal stability as falling into one of two classes (FIG. 10). In the first class (Mutation Class I, MC-I), mutation changes the interaction factors of the core residues and directly correlates with protein stability, since these changes bear directly on the most stabilizing section of the native state. This presumes that non-native folds involve different core residues and/or different conformations of these residues. As such, these mutations minimally change the non-native state energetics. In the second class (MC-II), mutation impacts interaction factors of surface residues or both surface and core residues and therefore perturbs either the non-native states or both native and non-native states. Whereas Class I mutations can be assessed by examining the ground state structure alone, Class II mutations do not necessarily lend themselves to reliable native state-based quantitative interpretation. Despite the difficulty of determining how a mutation may quantitatively impact alternative folds, the model can be used to qualitatively assess the impact of mutation (as Class I and Class II) and to quantitatively assess thermal stabilities of Class I mutations. The set of residues whose µ factor would change upon mutation of site i determines the thermal effect of a mutation. This may be called the member set of site i ($\theta_m^i$). Note that $\theta_m^i$ and $\theta_d^i$ may not necessarily be identical. The member set is composed of those residues whose µ values are impacted by mutation at site i, whereas the determinant set is composed of those residues that are normalized to give the µ value of site i. Analysis of the member set of each site can be used to assess whether a mutation will be of Class I or Class II, as illustrated below.

In an example embodiment, experimentally determined melting behavior of well-characterized single-site mutants of lysozyme were compared to the predicted thermal stability of these mutants. Accordingly, the σ-index profile for the folded protein was determined (as discussed above with respect to TABLE 3), the $\mu_i^o$ factors for the wildtype and mutant variants were determined, heat-maps of these proteins color-coded in accord with the $\mu_i^o$ factors were generated, and the data was used to qualitatively assess the expected correlation trends of 81 mutants at 13 sites of mutation, including the most stabilizing and destabilizing mutants.

Figure 11:
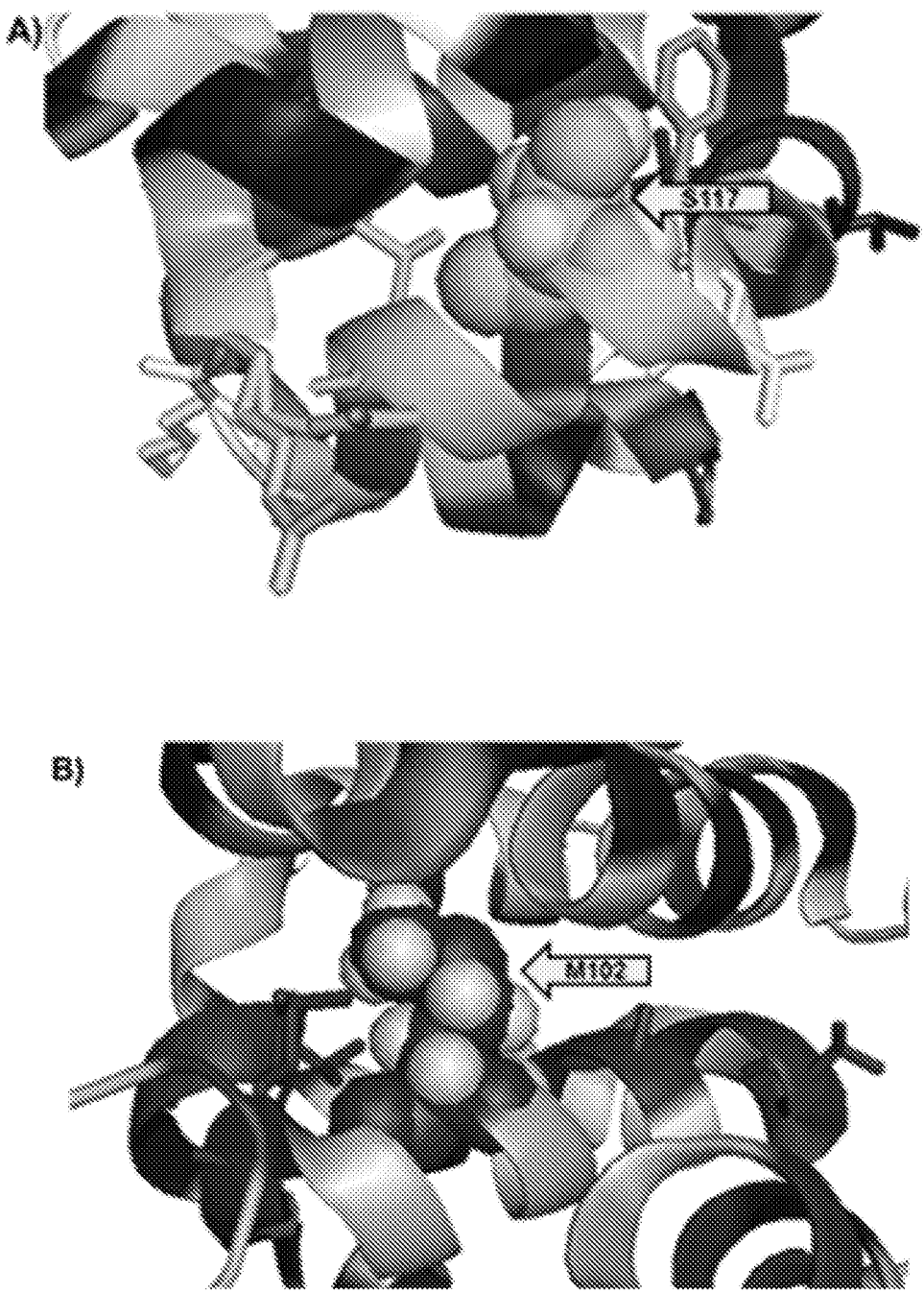
FIGS. 11A and 11B illustrate various regions of the heat-map of FIG. 7A in an enlarged form to provide a comparison of thermal stability of single-site mutants for a known structure of a T4 lysozyme protein, according to an embodiment ($\theta m$ sets for residues 117 (A) and 102 (B). Target residues are shown as space-filling spheres with grey hydrogen atoms, while other $\theta m$ set members have stick-form sidechains).

For example, as shown in FIG. 11A and FIG. 11B, the $\theta_m^i$ sets for each of thirteen positions of wild-type enzyme T4L mutation sites was mapped onto the native fold. Seven of the sites (3, 11, 115, 117, 119, 132, 133) were found to have $\theta_m$ sets that are dominated by buried residues, i.e. to MC-I mutations expected to contribute primarily to conformational ground state stabilization (FIGS. 11A and 11B). For example, residue S117 rests near the center of an α-helix (σ=4). The S117V mutant is the most stabilizing single point mutant known for T4L (ignoring disulfides). Position 117 is a member of the determinant set of sites 111(3), 114(3), 115(1), 117(4), 121(4), 124(1), and 125(1)$\in \theta_m^{117}$, where the number in parentheses indicates the σ-index of the residue). Consequently, mutation at 117 will impact the interaction factors of each member of this set in this fold. Many of the residues in $\theta_m^{117}$ are C-terminal core residues or contact these core residues, specifically sites 111, 114, 117, and 121. Therefore, mutation at 117 should bear primarily on ground state stability. Since the scale invariant term (γ) increases from serine to alanine to valine, the interaction factors for the entire $\theta_m^{117}$ set will increase for S117A and so will the expected thermal stability. The S117V mutant would be expected to increase in stability to an even greater extent. Similarly, residue M102 is buried, and the $\theta_m^{102}$ set includes some of the hottest C-terminal core residues in very close proximity to each other (94(4), 98(4), 102(4), 106(4), 110 (4), and 111(3)∈$\theta_m^{102}$, FIG. 11B). Mutation at this site is expected to bear primarily on ground state stability, and given the high scale invariant term for methionine most mutations at 102 would be expected to compromise stability. Hence, the model may be used to qualitatively assess the impact of the 13 point mutation sites, as MC-I or MC-II, and then to quantitatively assess expected change in folding free energy for the 30 mutants distributed across the seven MC-I sites ($\Delta\Delta G_{calc}$, FIG. 12).

Figure 12:
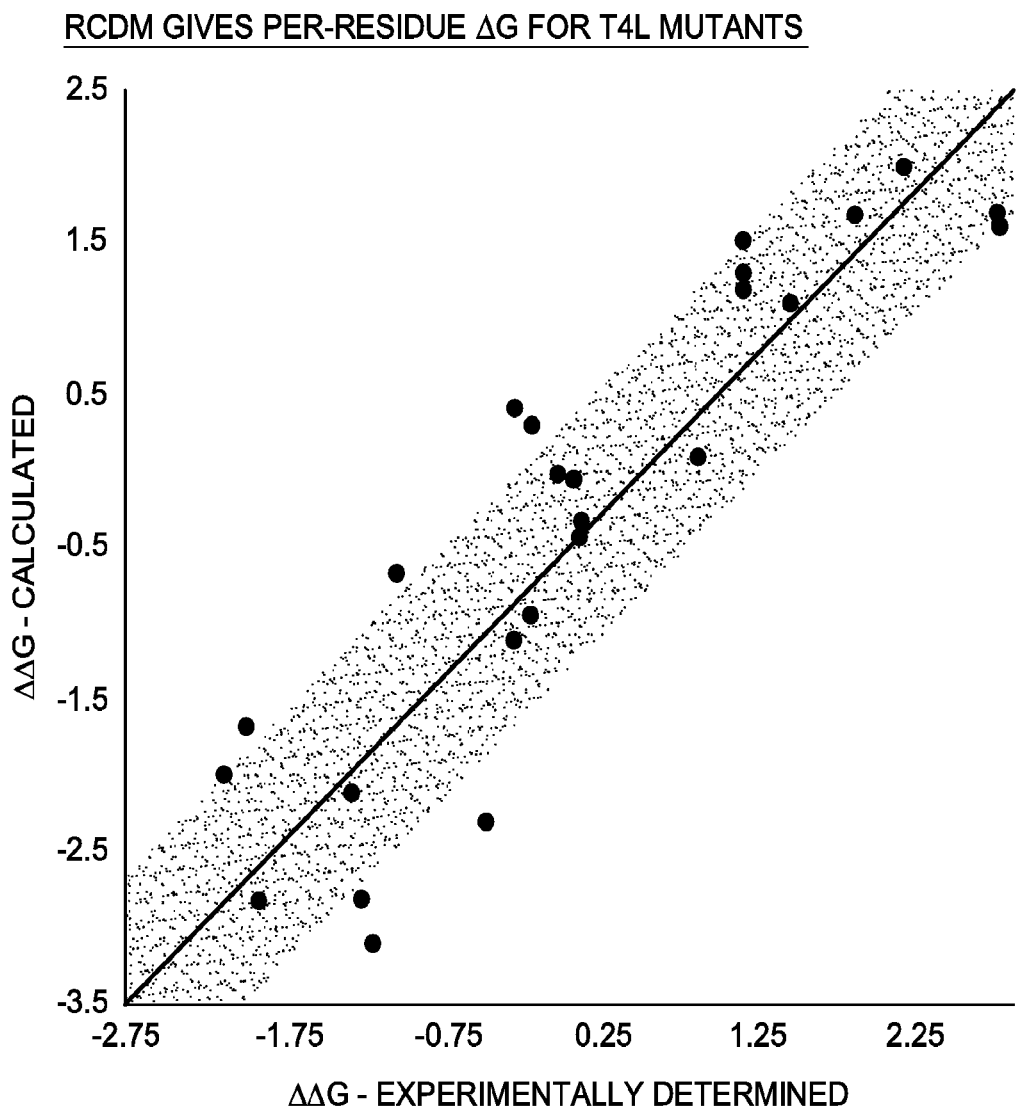
FIG. 12 illustrates a comparison of $\Delta\Delta G$folding of T4 bacteriophage lysozyme (T4L) for a set of known single point mutants with respect to experimentally determined values using the methods described in this document, according to an embodiment. ($R2=0.81$ (line), average unassigned error (AUE)=0.70 kcal/mol, AUE<1 kcal/mol=70% (grey band).
Figure 13:
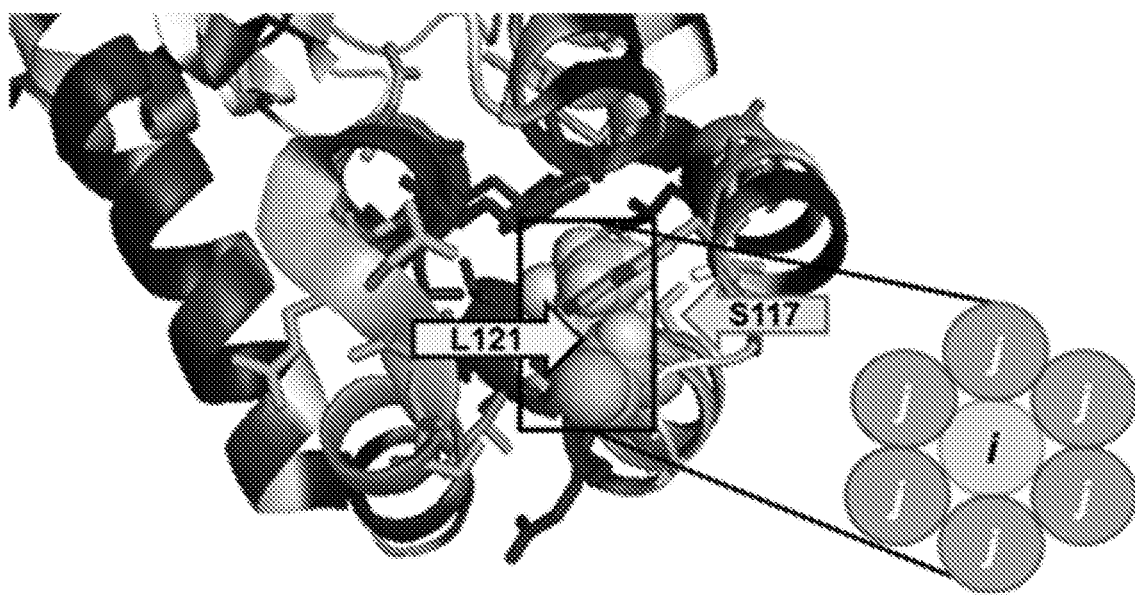
FIG. 13 illustrates a heat map and nearest contact neighbors for a mutant site of T4 lysozyme protein for the analysis of the thermal stability of the mutant site by determination pf protein interaction free energy of each residue determined by summing the interaction factor products of a residue within a $\theta m$ set (i) multiplied by its six nearest contact neighbors (j), according to an embodiment.

In an embodiment, the system may also quantitatively assess mutant thermal stability. The changes in folding free energy of the point mutations were calculated and compared to experimental data for the 30 well-characterized point mutants of T4L (FIG. 12). As described above, the free energy contributions are driven by the product of interaction factors ($\mu_i\mu_j$) of residue (i) and its nearest neighbors (j). The mutated residue and all residues whose potential energy is expected to be perturbed by the mutation (i.e. the θm residues of the mutation site) were evaluated. The neighbor residues of each of these positions were set to a maximum of six and defined by side chain/side chain proximity of up to approximately 3 Å. In the event that more than six neighbors were evident the six closest were selected. This process defines all the $\mu_i^o \mu_j^o$ pairs of the wildtype reference and all the corresponding $\mu_i^o \mu_j^o$ pairs that change upon mutation. The central residue corresponds to i in Equation 6 and the peripheral residues correspond to j. FIG. 13 illustrates the key aspects of the analysis with S117V. The S117V mutation significantly modulates the entire $\theta_m^{117}$ (FIG. 12). For example, L121 is one of the residues impacted by this mutation, since L121∈$\theta_m^{117}$ (FIG. 12). The six nearest neighbors with side chains within 3 Å of the L121 side chain are V87, L91, L118, W126, L133, and F153. The central residue corresponds to i in Equation 6 and the peripheral residues correspond to j. These data, the $\mu_i\mu_j$ factors, and the backbone and side chain entropy confinement penalties described by Baxa et al[43], and scaling factor λ gave $\Delta\Delta G_{calc}$ in very good agreement with experiments and showed a favorable comparison to calculations made using state of the art, all-atom full complexity descriptor (FCD) simulations like CHARMM36.

In an embodiment, the system may use the protein model to engineer proteins of a desired stability, characteristic, function, as well as manipulate, tune, and otherwise guide the engineering of proteins, peptides, small molecules for specific outcomes governed by interaction free energy. For example, proteins may be engineered by tuning or altering a protein's stability using one or mutations. The one or mutations may be configured to "cool" or "heat" interior or exterior residues of a protein. For example, one or more exterior residues of a protein may be mutated to cool down or heat up interior residues (as described for T4 lysozyme, residue S117), and the effect of such a mutation may be analyzed using the model described in this disclosure. In another example, one or more residues of a protein may be mutated to cool exterior residues in order to suppress protein aggregation. Aggregation can prevent effective expression of protein in both intracellular and cell-free expression systems, and hence suppression of aggregation may increase protein expression. Expression of proteins with attenuated protein aggregation profiles is highly valuable. The model may be used to quickly and simply evaluate surface variants less prone to aggregate. In yet another example, the model may be used to assess the impact of fusion of two proteins fused to each other.

Similarly, the model may be used to engineer proteins by mutation to manipulate residues involved in ligand binding. By cooling or heating interior or exterior residues of a protein, binding affinity of one or more regions of a protein be increased or decreased. Alternatively and/or additionally, mutants that will not impact binding may also be designed. For example, the model can be used to engineer a protein mutant that has superior solubility and/or is less likely to aggregate without impacting the function (binding of a native ligand, etc.) of the protein.

Example 4

Correlation Trends

In an embodiment, the system may also determine correlation trends corresponding to protein mutations. Given knowledge of which state, native or non-native, is most influenced by a mutation, free energy correlation trends may be predicted to be in one of three categories: positive, negative, or mixed. First, mutations that perturb native state free energies of the protein core (defined below) should positively correlate with protein stability. Second, mutations that perturb native state interaction free energy on the protein surface should negatively correlate with protein stability. Third, mutations that significantly mix perturbations of both native and non-native states will not lend themselves to straightforward interpretation by assessment of a single state.

It is important to recall that free energy contributions in step 114 of FIG. 1 are described on the residue scale and make no explicit reference to solvation, functional group interaction, etc. The term protein core as used in the context of the above method refers to the network of residues whose free energy contributions dominate the fold/microstate stability. Presumably, different folds of a given protein would involve different core residues and/or different conformations of the same residues. Whereas the core residues are buried in the protein interior, surface residues are those that are solvent exposed and coordinatively unsaturated. Exposed residues can interact with alternate or additional residues but to do so would require a change in conformation and a shift of the ensemble toward a different microstate. Among correlation trends, the first category corresponds to mutations that directly and significantly perturb the energetics of the native state and, as a consequence of different folds having different cores, minimally change the non-native state energetics. The second category focuses on instances where mutations significantly change the energetics of the non-native states and minimally change the native state. Decreasing the magnitude of per-residue interactions on the protein surface favors adoption of the native state by destabilizing alternative folds, especially non-native states that would bury (i.e. coordinatively saturate) these residues. Moreover, increasing the magnitude of native state surface residue interactions destabilizes the native state, because such mutations stabilize non-native states that would bury these residues or incorporate them into a different core. Despite the difficulty of quantitatively determining the relevant alternative fold energies, the trend is straightforward to identify qualitatively. Ambiguity necessarily arises when both the native and the non-native states are significantly perturbed. For example, mutations that influence networks that extend from the protein core to the surface are particularly problematic. The terms of the native state provide such a map of the energetics of the native state, and hidden symmetries combined with this map provide a means by which to predict energy correlation trends of mutation. Hence, the combination of the factors with confinement entropies provide a means by which to quantitatively assess mutation-induced free energy change.

Example 5

Qualitative U-Map Analysis

Consideration of the Hidden Symmetries of this protein fold defines expectations for mutation-thermal stability correlation trends. For example, residue S117 in FIG. 7E is shielded from solvent. In addition to a residue's elements of hidden symmetry ($\theta_d$=109, 113, 117, 121, 125), it is also a hidden symmetry set member ($\theta_m$) of other residues. For S117 these are residues $111_3$, $114_3$, $115_1$, $117_4$, $121_4$, $124_1$, and $125_1$ (the subscript indicates the σ-index of the indicated residue). Many of these are C-terminal core residues or are directly adjacent to such core residues (111, 114, 117, and 121). Therefore, mutation at 117 should positively correlate with the mutant amino acid gamma value (i.e., numerical descriptor). Residue M102 is shielded from solvent, one of the hottest residues in the protein, and—most importantly—the $\theta_m$ of this residue includes some of the hottest C-terminal core residues ($\theta_m$=$94_4$, $98_4$, $102_4$, $106_4$, $110_4$, and $111_3$). Clearly, mutation at 102 is expected to directly correlate with the gamma value of the mutant. Residue T115 is a $\theta_d$ member of many residues, ($\theta_m$=$107_4$, $112_3$, $115_1$, $119_4$, $123_4$, $124_1$, and $125_1$). The average $\mu_i^o$ factor for these highly solvent exposed residues is intermediate. Mutation at 115 should negatively correlate with the mutant gamma value. Residue N132 is a $\theta_d$ member of residues $124_1$, $125_1$, $128_4$, $132_4$, $136_4$, and $140_4$. Most of these are highly solvent exposed (124, 125, 128, 132, and 140). In contrast to residues discussed thus far, they are among the very lowest $\mu_i^o$ factors of the entire protein. Even maximal perturbations of these residues would be insignificant to the native state and would likely be insignificant to the non-native states. The lone exception is residue 136, which is buried in a network of relatively high potential residues. Hence, despite the mixed correlation trend, mutation of residue 132 should be dominated by residue 136 and thereby positively correlate with the gamma value of the mutant. Residue E11 is partially solvent exposed and a $\theta_d$ member of residues 34, 74, 114, 131, 154, and 194. Residues 3 and 7 have very high potentials, are buried, and constitute half of one of the hottest clusters (V, FIG. 9). The other residues, though partially solvent exposed, are in an environment of significant stabilization. Hence, mutation at 11 is expected to stabilize the non-native states to a much lesser degree than the native state, so a positive correlation with the mutant gamma value is expected. Finally, residue R96 is a $\theta_d$ member of residues $88_4$, $92_4$, $96_4$, $100_4$, and $104_4$. This group is remarkable because each of these residues are significantly solvent exposed, part of the same network, and, equally sensitive to perturbation by mutation at site 96. As such, mutations at 96 should synergistically stabilize the ground state and stabilize non-native states, especially since many of these residues already have high potentials and mutation from arginine to any residue other than lysine will only increase these potentials. Qualitative assessment predicts mixed correlation trends and indeterminate outcomes. All mutations in this study were assessed for expected correlation trends, and this qualitative analysis is in excellent agreement with quantitative comparisons to experimental data.

As will be appreciated by one skilled in the art, aspects of the present invention may be embodied as a system, a method, and/or a computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A data processing system suitable for storing and/or executing program code may include at least one processor, which may be or be part of a controller, coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

It will be clear that the various features of the foregoing systems and/or methodologies may be combined in any way, creating a plurality of combinations from the descriptions presented above.

It will be further appreciated that embodiments of the present invention may be provided in the form of a service deployed on behalf of a customer to offer service on demand.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. A method for modeling a three-dimensional protein structure, the method comprising:
receiving a primary amino acid sequence of a three-dimensional protein;
translating the primary amino acid sequence to a first vector, wherein the first vector comprises a unique numerical descriptor value corresponding to each amino acid residue in the primary amino acid sequence;
determining a per-residue conformation index for each amino acid residue in the primary amino acid sequence;
determining a vector set for each amino acid residue in the primary amino acid sequence, wherein the vector set comprises a plurality per-residue interaction factors corresponding to a plurality of conformation indexes for that amino acid residue; and
using the per-residue interaction vector set to generate a multi-dimensional matrix for the three-dimensional protein structure,
wherein the numerical descriptor value is a fractal exponent value, and
wherein the per-residue conformation index for each amino acid residue in the primary amino acid sequence is used to represent a Closest-Linked Nearest Neighbors (clNN) relationship for that amino acid residue.

2. The method of claim 1, wherein the vector set for the amino acid residue is also a function of a normalization length of the protein.

3. The method of claim 2, wherein the normalization length is equal to 10.

4. The method of claim 1, wherein the numerical descriptor value corresponding to each amino acid residue in the primary amino acid sequence is determined as a function of a solvent accessible surface area of that amino acid residue.

5. The method of claim 1, wherein the first vector is a scale-invariant vector.

6. The method of claim 1, wherein translating the primary amino acid sequence to the first vector comprises replacing each amino acid residue in the primary amino acid sequence with a corresponding numerical descriptor value.

7. The method of claim 1, wherein the multi-dimensional matrix comprises a plurality of per-residue interaction factors corresponding to one or more amino acids in the primary amino acid sequence and representing all conformations of the primary amino acid sequence.

8. The method of claim 1, further comprising determining a free energy of one or more interacting pairs of amino acid residues in the primary amino acid sequence by determining the free energy as a function of the per-residue interaction vector set corresponding to each of the amino acid residues of an interacting pair of amino acids.

9. The method of claim 8, further comprising modeling the three-dimensional protein structure as a function of one or more of the following: a plurality of vector sets corresponding to amino acid residues in the primary amino acid sequence, or the free energy of one or more interacting pairs of amino acid residues in the primary amino acid sequence.

10. The method of claim 9, further comprising generating a graphical representation of the modeled three-dimensional protein structure.

11. The method of claim 10, wherein generating the graphical representation comprises generating a plot of per-residue interaction factors of the primary amino acid sequence for a structural configuration of the three-dimensional protein, wherein generating the plot comprises: selecting a plurality of per-residue interaction factors from the multi-dimensional matrix based on the structural configuration; and using the selected plurality of per-residue interaction factors to generate the plot.

12. The method of claim 11, further comprising classifying each of the amino acid residues of the primary amino acid sequence into one of two or more categories based on a corresponding value of the per-residue interaction factor.

13. The method of claim 10, wherein generating the graphical representation comprises generating an energy map for a structural configuration of the three-dimensional protein.

14. The method of claim 13, wherein the structural configuration is a native configuration of the three-dimensional protein.

15. The method of claim 9, further comprising using the modeled three-dimensional protein structure to determine a structure of the three-dimensional protein that has enhanced stability.

16. The method of claim 9, further comprising using the modeled three-dimensional protein structure for engineering a new protein configured to bind to a target molecule.

17. A method for modeling a three-dimensional protein structure, the method comprising:
  receiving a primary amino acid sequence of a three-dimensional protein;
  translating the primary amino acid sequence to a first vector, wherein the first vector comprises a unique numerical descriptor value corresponding to each amino acid residue in the primary amino acid sequence;
  determining a per-residue conformation index for each amino acid residue in the primary amino acid sequence;
  determining a vector set for each amino acid residue in the primary amino acid sequence, wherein the vector set comprises a plurality per-residue interaction factors corresponding to a plurality of conformation indexes for that amino acid residue;
  using the per-residue interaction vector set to generate a multi-dimensional matrix for the three-dimensional protein structure; and
  using the multi-dimensional matrix to determine a structure of the three-dimensional protein that has enhanced stability,
  wherein the numerical descriptor value is a fractal exponent value, and
  wherein the per-residue conformation index for each amino acid residue in the primary amino acid sequence is used to represent a Closest-Linked Nearest Neighbors (clNN) relationship for that amino acid residue.

* * * * *